United States Patent
Backman et al.

(10) Patent No.: US 7,667,832 B2
(45) Date of Patent: Feb. 23, 2010

(54) SYSTEM FOR IDENTIFYING REFRACTIVE-INDEX FLUCTUATIONS OF A TARGET

(75) Inventors: Vadim Backman, Chicago, IL (US); Yang Liu, Somerset, NJ (US); Young Kim, West Lafayette, IN (US)

(73) Assignees: Northwestern University, Evanston, IL (US); NorthShore University HealthSystem, Evanston, IL (US)

( * ) Notice: Subject to any disclaimer, the term of this patent is extended or adjusted under 35 U.S.C. 154(b) by 0 days.

(21) Appl. No.: 11/891,884

(22) Filed: Aug. 13, 2007

(65) Prior Publication Data

US 2008/0180664 A1     Jul. 31, 2008

Related U.S. Application Data

(60) Provisional application No. 60/837,103, filed on Aug. 11, 2006, provisional application No. 60/837,052, filed on Aug. 11, 2006.

(51) Int. Cl.
 *G01N 21/41* (2006.01)
(52) U.S. Cl. .................................... 356/128
(58) Field of Classification Search ................ 356/326, 356/317, 128
See application file for complete search history.

(56) References Cited

U.S. PATENT DOCUMENTS

| | | | |
|---|---|---|---|
| 5,037,202 A | 8/1991 | Batchelder et al. | |
| 5,303,024 A | 4/1994 | Thierman | |
| 5,650,847 A | 7/1997 | Maltsev et al. | |
| 5,799,656 A | 9/1998 | Alfano et al. | |
| 6,320,660 B1 * | 11/2001 | Ju et al. | 356/417 |
| 6,405,070 B1 | 6/2002 | Banjeree | |
| 6,639,674 B2 | 10/2003 | Sokolov et al. | |
| 6,650,357 B1 | 11/2003 | Richardson | |
| 6,922,583 B1 | 7/2005 | Perelman et al. | |
| 6,927,860 B2 | 8/2005 | Podoleanu et al. | |
| 7,061,622 B2 | 6/2006 | Rollins et al. | |
| 2003/0215846 A1 | 11/2003 | Watt et al. | |
| 2004/0189987 A1 * | 9/2004 | Bondurant et al. | 356/241.1 |

(Continued)

OTHER PUBLICATIONS

Adam Wax, et al., "Cellular Organization and Substructure Measured Using Angle-Resolved Low-Coherence Interferometry", Biophysical Journal, Apr. 2002, pp. 2256-2264, vol. 82.

(Continued)

*Primary Examiner*—Tarifur Chowdhury
*Assistant Examiner*—Abdullahi Nur
(74) *Attorney, Agent, or Firm*—Paul, Hastings, Janofsky & Walker LLP

(57) ABSTRACT

Systems and methods for identifying refractive-index fluctuations of a target are described in this application. One embodiment includes identifying one or more properties of emergent light, the emergent light to be emergent from a target, and determining refractive-index fluctuations of the target based on the one or more properties of the emergent light. The determining refractive-index fluctuations further comprises determining one or more of the variance of the refractive-index fluctuations and the spatial correlation length of the refractive-index fluctuations. The determining refractive-index fluctuations further comprises determining one or more of the variance of the refractive-index fluctuations and the spatial correlation length of the refractive-index fluctuations.

20 Claims, 21 Drawing Sheets

U.S. PATENT DOCUMENTS

| | | | |
|---|---|---|---|
| 2004/0223162 | A1 | 11/2004 | Wax |
| 2005/0046821 | A1* | 3/2005 | Hanson et al. ............. 356/3.01 |
| 2005/0265586 | A1 | 12/2005 | Rowe et al. |
| 2007/0201033 | A1 | 8/2007 | Desjardins et al. |

OTHER PUBLICATIONS

Irving Itzkan et al., "Confocal light absorption and scattering spectroscopic microscopy monitors organelles in live cells with no exogenous labels", Proceedings of the National Academy of Sciences, Oct. 30, 2007, pp. 17255-17260, vol. 104, No. 44.

Hariharan Subramanian et al., "Nanoscale Cellular Changes in Field Carcinogenesis Detected by Partial Wave Spectroscopy", American Association for Cancer Research Journal, Jul. 1, 2009, pp. 5357-5363.

Hariharan Subramanian et al., "Optical methodology for detecting histologically unapparent nanoscale consequences of genetic alterations in biological cells", Proceedings of the National Academy of Sciences, Dec. 23, 2008, pp. 20124-20129, vol. 105, No. 51.

Hariharan Subramanian et al., "Partial-wave microscopic spectroscopy detects subwavelength refractive index fluctuations: an application to cancer diagnosis" Optics Letters, Optical Society of America, Feb. 15, 2009, pp. 518-520, vol. 34, No. 4.

Yang Liu et al., "Elastic backscattering spectroscopic microscopy", Optic Letters, Optical Society of America, Sep. 15, 2005, pp. 2445-2447, vol. 30, No. 18.

Young L. Kim et al., "Low-coherent backscattering spectroscopy for tissue characterization", Applied Optics, Jan. 20, 2005, pp. 366-377, vol. 44, No. 3.

Young L. Kim et al., "Coherent backscattering spectroscopy", Optics Letters, Optical Society of America, Aug. 15, 2004, pp. 1906-1908, vol. 29, No. 16.

Young L. Kim et al., "Low-coherence enhanced backscattering: review of principles and applications for colon cancer screening", Journal of Biomedical Optics, Jul./Aug. 2006, pp. 041125-1-041125-10, vol. 11(4).

Young L. Kim et al., "Depth-resolved low-coherence enhanced backscattering", Optics Letters, Optical Society of America, Apr. 1, 2005, pp. 741-743, vol. 30, No. 7.

International Preliminary Report on Patentability dated Feb. 26, 2009 from PCT/US07/017894.

International Search Report and Written Opinion dated Mar. 19, 2008 from PCT/US07/017894.

Ingle, James D. et al., Spectrochemical Analysis, Prentice-Hall Inc., 1988, ISBN 0-13-826876-2 p. 520.

Ramanujam, Nirmala, Flourescence Spectrocopy of Neoplastic and Non-Neoplastic Tissues, Neoplasma, Neoplasma Press, Inc., Jan. 2000, V. 2(102), p. 89-117.

Brownson, RC et al., Family history of cancer and risk of lung cancer in lifetime non-smokers and long-term ex-smokers, Int J. Epidemiol, Apr. 1997, vol. 26, No. 2, p. 256-263 (abstract).

International Search Report and Written Opinion dated Jul. 22, 2008 from PCT/US07/11404.

International Preliminary Report on Patentability dated Nov. 17, 2008 from PCT/US07/11404.

Wolf, P.E., Maret, G., Akkermans, E. & Maynard, R., "Optical Coherent Backscattering by Random-Media—an Experimental-Study." Journal de Physique 49, 63-75 (1988).

Yoo, K. M., Tang, G.C., and Alfano, R.R., "Coherent Backscattering of Light from Biological Tissues." Applied Optics 29, 3237-3239 (1990).

Chen, L.C., Hao, C. Y., and Chiu, Y. C., et al., "Alteration of gene expression in normal-appearing colon mucosa of APCminmice and human cancer patients." Cancer Res 64, 3694-700 (2004).

Liu, Y., Kim, Y. L., Li, X., and Backman, V. Investigation of depth selectivity of polarization gating for tissue characterization. Opt. Express, 13: 601-611, 2005.

Roy, H. K., Kim, Y. L., Liu, Y., Wali, R. K., Goldberg, M. J., Turzhitsky, V., Horwitz, J., and Backman, V. "Risk stratification of colon carcinogenesis through enhanced backscattering (EBS) spectroscopy analysis of the uninvolved colonic mucosa," Clinical Cancer Research 12(3), 961-968 (2006).

Siegel, M. P., Kim, Y. L., Roy, H., Wali, R., and Backman, V. "Assessment of Blood Supply in Superficial Tissue using Polarization Gated Elastic Light Scattering Spectroscopy," Appl Optics, accepted 45(2), 335-342 (2006).

Wali, R. K., Roy, H. K., Kim, Y. L., Liu, Y., Koetsier, J. L., Kunte, D. P., Goldberg, M. J., Turzhitsky, V., and Backman, V. "Increased Microvascular Blood Content is an Early Event in Colon Carcinogenesis," Gut 54, 654-660 (2005).

Kim, Y., Liu, Y., Wali, R. K., Roy, H. K., Goldberg, M. J., Kromine, A. K., Chen, K., and Backman, V. "Simultaneous measurement of angular and spectral properties of light scattering for characterization of tissue microarchitecture and its alteration in early precancer," IEEE J. Sel. Top. Quantum Electron. 9, 243-257 (2003).

Kim, Y. L., Pradhan, P., Subramanian, H., Liu, Y., Kim, M. H., and Backman, V. "Origin of low-coherence enhanced backscattering," Optics Letters 31(10), 1459-1461 (2006).

Stephen B. Haley et al., "Wave propagation in one-dimensional disordered structures", The American Physical Society, Physical Review B, Apr. 15, 1992, pp. 8572-8584, vol. 45, No. 15.

Kumar, N., "Resistance fluctuation in a one-dimensional conductor with static disorder", The American Physical Society, Physical Review B, Apr. 15, 1985, pp. 5513-5515, vol. 31, No. 8.

\* cited by examiner

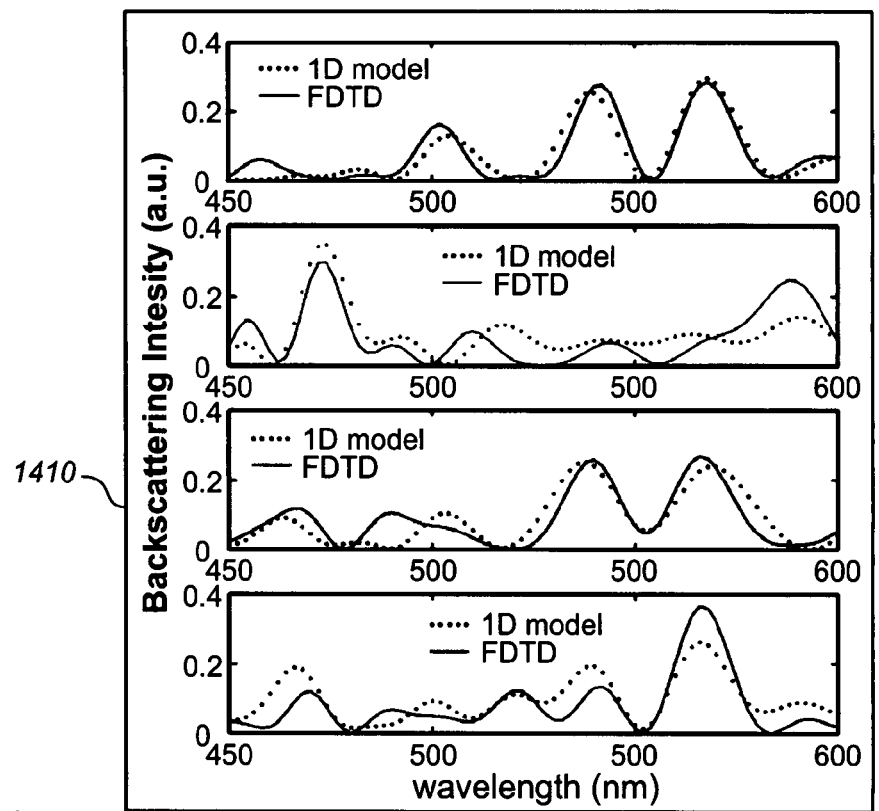
FIGURE 14B
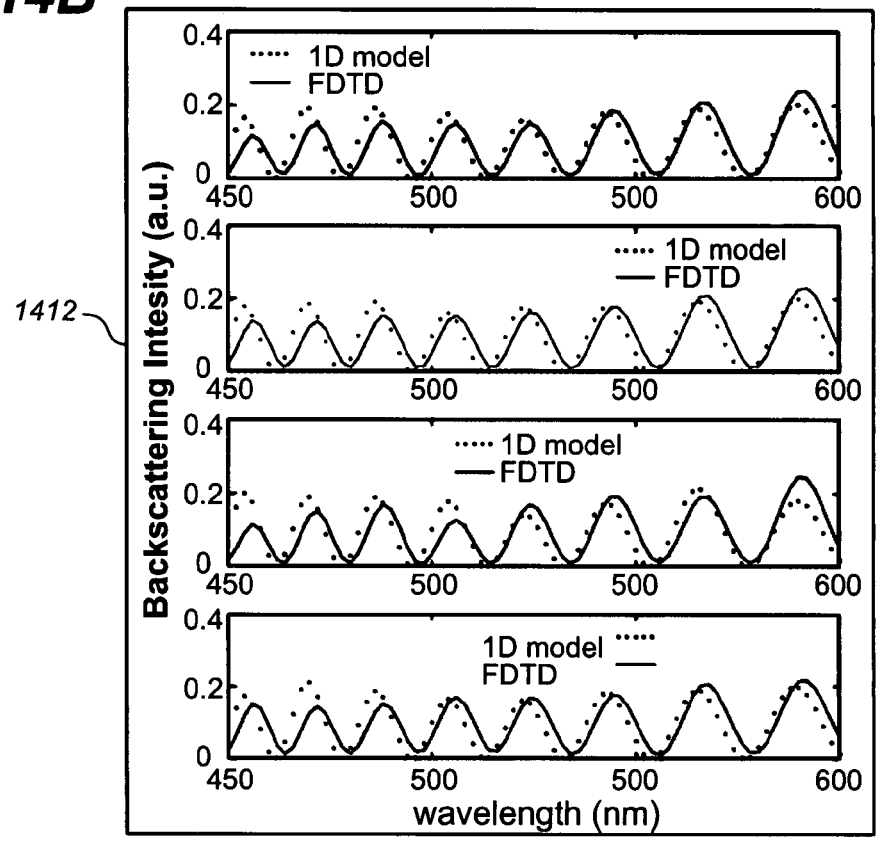

PWS on Cytologically Malignant Pancreatic Cancer Cells

PWS on Cytologically Normal Pancreatic Cancer Cells

SYSTEM FOR IDENTIFYING REFRACTIVE-INDEX FLUCTUATIONS OF A TARGET

CLAIM OF PRIORITY

This application claims priority to U.S. Patent Application No. 60/837,103 entitled "Apparatus and Methods of Partial Wave Spectroscopy", which was filed on Aug. 11, 2006, the contents of which are expressly incorporated by reference herein. This application further claims priority to U.S. Patent Application No. 60/837,052 entitled "Apparatus and Methods of Ultra-Early Detection of Carcinogenesis in a Single Cell Via Partial Wave Spectroscopy", which was filed on Aug. 11, 2006, the contents of which are expressly incorporated by reference herein.

CROSS-REFERENCE TO RELATED PATENT APPLICATIONS

This application is related to a copending U.S. patent application Ser. No. 11/261,452, entitled "MULTI-DIMENSIONAL ELASTIC LIGHT SCATTERING", filed 27 Oct. 2005 with the same assignee as the present disclosure. The disclosure of the above identified copending application is incorporated in its entirety herein by reference.

This application is related to a copending U.S. patent application Ser. No. 11/604,653, entitled "METHOD OF RECOGNIZING ABNORMAL TISSUE USING THE DETECTION OF EARLY INCREASE IN MICROVASCULAR BLOOD CONTENT", filed 27 Nov. 2005 with the same assignee as the present disclosure claiming priority to U.S. Application No. 60/801,947 entitled "GUIDE-TO-COLONOSCOPY BY OPTICAL DETECTION OF COLONIC MICRO-CIRCULATION AND APPLICATIONS OF THE SAME", filed 19 May 2006. The disclosure of the above identified copending applications is incorporated in its entirety herein by reference.

This application is further related to a copending U.S. patent application Ser. No. 11/604,659, entitled "APPARATUS FOR RECOGNIZING ABNORMAL TISSUE USING THE DETECTION OF EARLY INCREASE IN MICROVASCULAR BLOOD CONTENT", filed 27 Nov. 2005 with the same assignee as the present disclosure claiming priority to U.S. Application No. 60/801,947 entitled "GUIDE-TO-COLONOSCOPY BY OPTICAL DETECTION OF COLONIC MICRO-CIRCULATION AND APPLICATIONS OF THE SAME", filed 19 May 2006. The disclosure of the above identified copending applications is incorporated in its entirety herein by reference.

This application is further related to a copending U.S. patent application, entitled "SYSTEMS, METHODS, AND APPARATUSES OF ELASTIC LIGHT SCATTERING SPECTROSCOPY AND LOW-COHERENCE ENHANCED BACKSCATTERING SPECTROSCOPY", filed 11 May 2007 with the same assignee as the present disclosure claiming priority to U.S. Application No. 60/801,954 entitled "FOUR-DIMENSIONAL ELASTIC LIGHT SCATTERING SPECTROSCOPY, LOW-COHERENCE ENHANCED BACKSCATTERING SPECTROSCOPY, RELATED OPTICAL MARKERS, AND APPLICATIONS OF SAME", filed 19 May 2006. The disclosure of the above identified copending applications is incorporated in its entirety herein by reference.

This application is further related to a copending U.S. patent application, entitled "SYSTEMS, METHODS, AND APPARATUSES OF LOW-COHERENCE ENHANCED BACKSCATTERING SPECTROSCOPY", filed 11 May 2007 with the same assignee as the present disclosure claiming priority to U.S. Application No. 60/799,970 entitled "Low-Coherence Enhanced Backscattering Spectroscopy and Applications of Same", filed 12 May 2006. The disclosure of the above identified copending applications is incorporated in its entirety herein by reference.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FEDERALLY-SPONSORED RESEARCH

This disclosure was made with Government support under Grant No. R01 EB003682, and R01 CA112315, awarded by the National Institutes of Health of the United States, and Grant Nos. CBET-0238903, and CBET-0417689 awarded by the National Science Foundation of the United States. Accordingly, the United States Government may have certain rights in this disclosure pursuant to these grants.

THE TECHNICAL FIELD

The present disclosure relates generally to light scattering, and in particular to elastic light scattering and/or applications of light scattering including medical diagnostic and treatment purposes.

BACKGROUND

Structural aberrations (dysplasia-carcinoma sequence) during neoplastic transformation typically occur relatively late in the process of carcinogenesis with the earlier stages generally silent from a pathological perspective. From a clinical perspective (e.g., in cytological diagnosis), it is desirable to identify earlier stages of carcinogenesis. At early stages, genetic/epigenetic changes may not yet have translated into microscopic consequences, although the fundamental nanoscale architecture of these cells may be perturbed during early neoplastic transformation.

Physical and technological limitations have stymied understanding of changes in cell organization at a submicron scale (e.g., at the nanoscale). For example, the capability of existing optical imaging techniques may be restricted by diffraction-limited resolution. In addition, available imaging techniques are typically unable to quantitatively characterize nanoscale organization of living cells and tissue in a nondestructive manner.

Colorectal cancer remains one of the leading causes of cancer mortality in the United States. In 2006, there were approximately 55,170 estimated colorectal cancer (CRC) related deaths. Given early detection, early-stage colorectal cancer can be curable. However, given the nature of colonic neoplasia, most patients are diagnosed when the cancer has evolved to a more advanced stage thus underscoring the need for effective screening of the at-risk population (e.g., those over 50 years of age) for early detection. For example, existing colorectal cancer screening methods include fecal blood tests (FOBTs), endoscopy for direct visualization of the colon (e.g., flexible sigmoidoscopy or colonoscopy), and/or air-contrast barium enema. Although, the existing methods have demonstrated some efficacy in reducing colorectal cancer mortality and incidence, a large portion of the population do not undergo any endoscopic screening potentially due to patient and/or physician reluctance.

However, due to resource constraints and potential complications, performing colonoscopy on an entire at-risk population (e.g., those over the age of 50) may be impractical. In addition, for the general population the lifetime risk of developing CRC is approximately 6%. Thus performing colonoscopy on a large population to reach a relatively small subgroup of the at risk population who may develop colonic neoplasia is cost and time inefficient. Numerous techniques have been introduced for colorectal cancer screening but have yet to demonstrate the robustness suitable for population screening. For example, reports of demonstrated performance of fecal DNA analysis were not statistically significant in multicenter trials. Further, the marked cost of fecal DNA analysis may be a barrier to wide spread usage. From a radiological perspective, in single center studies, computed tomography colography (virtual colonoscopy) showed promise; unfortunately, the sensitivity demonstrated in multicenter trials have been unreliable.

Thus, there is a need to identify patients with a higher likelihood of harboring colonic neoplasia to provide colonoscopy to a better defined set of patients more likely to be harboring neoplasia thereby sparing those patients who are unlikely to benefit from the cost, inconvenience, and potential complication of colonoscopy.

In addition, pancreatic cancer is another leading cause of cancer death in the United States with most cancers diagnosed at a late, incurable stage. Existing approaches, including high-resolution imaging (MRI, CT, etc.), molecular diagnostics, and/or endoscopic cholangiopancreatography (ERCP), have not demonstrated the robustness for detecting early pancreatic neoplasm for allowing effective treatment.

Current imaging modalities as well as ERCP utilize detection of the presence of a mass lesion, and, therefore the detected tumors are typically biologically too advanced for cure. Despite years of research no clinically adequate molecular markers have been developed. The only route that currently has the potential for diagnosing pre-invasive cancer is through the pancreatic duct, where 90% of adenoma or carcinomas of the pancreas originate. Due to the potential for complications including pancreatitis (3-5% cases), as currently performed, ERCP may not be suitable for routine screening over successive points in time.

SUMMARY OF THE INVENTION

The invention includes, in part, systems and methods for identifying refractive-index fluctuations of a target, which are described here. Some embodiments of the present disclosure are summarized in this section.

In one aspect, embodiments of the present disclosure include a method, which may be implemented on a system, of identifying one or more properties of light, which is emergent from a target, either by backscattering or through-transmission, and determining refractive-index fluctuations of the target based on the one or more properties of the emergent light. In one embodiment, the one or more properties of the emergent light comprise a measure of the reflectivity of the emergent light. In a further embodiment, the measure of the reflectivity comprises a measure of the high-frequency spectral component of the emergent light. The measure of the reflectivity of the emergent light may comprise the difference of the emergent spectra and a low-frequency spectral component of the emergent spectra. In one embodiment the one or more properties of the emergent light comprise an autocorrelation of the measure of the reflectivity of the emergent light. The step of determining the refractive-index fluctuations may further comprise the step of determining one or more of the variance of the refractive-index fluctuations and the spatial correlation length of the refractive-index fluctuations.

In one aspect, embodiments of the present disclosure include a method, which may be implemented on a system, of providing incident light comprising at least one spectral component, wherein the incident light is to be illuminated on the target, recording the intensity of one or more preselected spectra of light which has been backscattered from or transmitted through the target, wherein a spectrum of the one or more preselected spectra corresponds to the emergent light from one or more preselected portions of a target, and analyzing the intensity of the one or more preselected spectra of emergent light towards evaluating the properties of the illuminated portion of the target; wherein the properties to be evaluated for the target, are for one or more portions of the target.

One embodiment further includes, recording an image formed by the emergent light of the illuminated portion of the target. The properties may include one or more of the size of particles, the concentration of particles, the refractive index, the spatial distribution of refractive indices, and the spatial distribution of the concentration of particles, of the target. In one embodiment, a beam diameter of the incident light is substantially larger than the target such that the incident light corresponds to a plane wave at the target. The incident light may include white light.

One embodiment further includes the step of identifying a single scattering particle of the target. The embodiment may further include the steps of recording the intensity of a first set of spectra of emergent light from a periphery of a particle of the target and recording the intensity of a second set of spectra of emergent light from a center of the particle of the target. The embodiment may further include the steps of determining the size of the particle via analyzing the intensity of the second set of spectra of emergent light recorded from the center of the particle and determining the diameter of the particle via curve fitting the second spectrum of the emergent light recorded from the center of the particle to a spectrum computed based on a uniform slab model.

One embodiment further includes identifying a localized scattering particle of an aggregation of densely packed particles of the target. The embodiment may further include the step of determining one or more statistical attributes related to the intensity of the one or more spectra of the emergent light. The at least one statistical attribute may comprise one or more of a probability density distribution of a reflection coefficient, an autocorrelation function of the reflection coefficient, a disorder strength the standard deviation of the disorder strength, and the probability density of the disorder strength. In one embodiment, the reflection coefficient is a measure of the high-frequency spectral component of the emergent light.

One embodiment further includes the step of determining the reflection coefficient via obtaining a difference between the intensity of the emergent light and a slow varying component of the intensity of the emergent light normalized by the intensity of the incident light, for the one or more spectra of the emergent light. The embodiment may further include the step of determining the disorder strength from the reflection coefficient and the autocorrelation function of the reflection coefficient of the one or more spectra of the emergent light. The disorder strength can be a measure of one or more of a variance of refractive-index fluctuations and a spatial correlation length of the refractive-index fluctuations. In one embodiment, the method may comprise the step of determining statistical parameters of the disorder strength. The statistical parameters may include one or more of a disorder strength and a standard deviation of the disorder strength averaged over a predetermined area, wherein the predetermined area corresponds substantially to an area of a cell. The statistical parameters may include one or more of a mean and a standard deviation for a predetermined percentile of the disorder strength over the area of the cell. The statistical parameters may also include one or more of the mean disorder strength and the standard deviation of the disorder strength, averaged over a plurality of cells. The statistical parameters may also include one or more of a standard deviation of, the mean disorder strength and the standard deviation of the disorder strength, over a plurality of cells.

In one embodiment, the plurality of cells are at least a portion of a cytological sample. The plurality of cells may be one or more of fixed cells, living cells, and/or stained cells. The size of the preselected portion of the target from which the emergent light originates, which may be limited by the diffraction-limit of the resolution of the imaging system, may be on the order of a microscale. In one embodiment, the target is a biological sample. The target may further be at least a portion of the living subject. In addition, the biological sample is at least a portion of a cytological preparation. The biological tissue may include tissue undergoing neoplastic transformation.

One embodiment may include the step of evaluating the physical properties for a localized region of the tissue. The physical properties to be evaluated for the tissue, may be for one or more portions of the tissue of a scale on the order of the area of one or more cells. The embodiment may further include the step of evaluating the physical properties of a single cell of the tissue, such as detecting alteration in the cellular architecture of the single cell. The alteration may correspond to a cancerous alteration. The cancerous alteration may correspond to pancreatic cancer, colon cancer, liver cancer, lung cancer, esophageal cancer, stomach cancer, cervical cancer, oral cavity cancer, ovarian cancer, breast cancer, bladder cancer, cholangiocarcinoma, prostate cancer, and/or head and neck cancer. The target may be obtained from an endoscopically normal biological sample, a histologically normal biological sample, and a cytologically normal biological sample.

In one embodiment, the target comprises non-neoplastic tissue to detect one or more of adenoma and carcinoma of tissue obtained from a different anatomic portion than the non-neoplastic tissue. For example, the target comprises tissue of an anatomical region of at least one of a proximal and distal to tissue of the anatomical region potentially harboring one or more of adenoma and carcinoma. In one embodiment, the method further includes detecting presence of one or more of adenoma and carcinoma in at least a part of the colon based on identification of properties of tissue obtained from anywhere in the colon. The tissue that can be obtained from the anywhere in the colon comprises at least one of a cecum, ascending colon, hepatic flexure, transverse colon, splenic flexure, descending colon, sigmoid colon, and rectum.

One embodiment further comprises detecting pancreatic neoplasia via analyzing the intensity of the one or more spectra of emergent light from non-neoplastic tissue. The non-neoplastic tissue may, in some instances, be duodenal periampullary mucosa. The non-neoplastic tissue may be any tissue affected by at least one of a genetic and environmental milieu to result in the pancreatic neoplasia. One embodiment further includes detecting lung cancer via analyzing the intensity of the one or more spectra of emergent light from non-neoplastic tissue. The non-neoplastic tissue can be buccal mucosa. The embodiment may further include the steps of distinguishing a patient with lung cancer among a set of patients with chronic obstructive pulmonary disease and/or distinguishing a patient with a family history of lung cancer among the set of patients with chronic obstructive pulmonary disease. The set of patients may be smokers. One embodiment includes identifying different genetic variations of a cell such as different genetic variations of an HT29 cell.

In another aspect, embodiments of the present disclosure include a system including a light source to provide incident light having at least one spectral component, a first set of one or more optical components operatively configured to collimate the incident light, a second set of one or more optical components operatively configured to focus the incident light on the target, and a receiving end to record the intensity of one or more preselected spectra of emergent light, the emergent light to be emergent from illumination of the incident light on an illuminated portion of the target.

In one embodiment, the diameter of a beam of light illuminated on the target is substantially larger than a size of the target such that the beam of light illuminated on the target corresponds to a plane wave. In one embodiment, the light source comprises a white light source. The light source may obtain the at least one spectral components of light from a plurality of narrowband light sources. The light source may be one or more of an arc-lamp, a white light emitting diode, a laser source, and a color light emitting diode. The laser source may include one or more lasers with one or more wavelengths of emission. In one embodiment, the color light emitting diode may further include one or more light emitting diodes with one or more spectral emission ranges.

In one embodiment, the first set of one or more optical components comprises a 4-f system and an aperture. For example, the 4-f system may be a two lens 4-f system. In one embodiment, the lens is a positive lens. Additionally, the lens can be a Fourier lens, a ball lens, a graded refractive index lens, an aspheric lens, cylindrical lens, convex-convex lens, and/or plano-convex lens. Further, the aperture may be, in one embodiment, disposed substantially in a common focal plane of the two lenses. In one embodiment, the system includes a condenser disposed between the light source and the 4-f system.

In one embodiment, the receiving end comprises an imaging spectrograph. The receiving end further may further include a light detector to record an image of the emergent light from the target. In addition, the light detector may be coupled with the imaging spectrograph, and a scanning stage may be coupled with the image spectrograph and the light detector, the scanning stage operatively configured to move about a predetermined position. The light detector may be a CCD camera. In one embodiment, the light detector can be a plurality of photodetectors.

In one embodiment, the second set of the one or more optical components comprises an objective lens. The emergent light may be collected by the objective lens. The embodiment may further include a tube lens to focus the emergent light collected by the objective lens to magnify the image of the emergent light and a flipper mirror operatively configured to deflect the emergent light collected by the objective lens. The flipper mirror can be operatively configured to deflect the emergent light to a camera to visualize an image before it is recorded. In one embodiment, the target may include one or more living cells of a biological sample.

In one embodiment, the receiving end may further comprise one or more single channel linear-array spectrometers and/or filters to record an intensity of one or more of at least one spectral component of emergent light. The filter may a tunable filter, a filter wheel, and/or dichronics.

The present disclosure includes methods and systems which perform these methods, including processing systems which perform these methods, and computer readable media which when executed on processing systems cause the systems to perform these methods.

Other features of the present disclosure will be apparent from the accompanying drawings and from the detailed description which follows.

BRIEF DESCRIPTION OF THE DRAWINGS

FIG. 14B illustrates plots to compare the spectra obtained from FDTD simulations and the 1D slab model for analyzing the backscattered spectrum of a portion of the image obtained from partial wave spectroscopy, according to one embodiment.

DETAILED DESCRIPTION OF THE INVENTION

Figure 1:
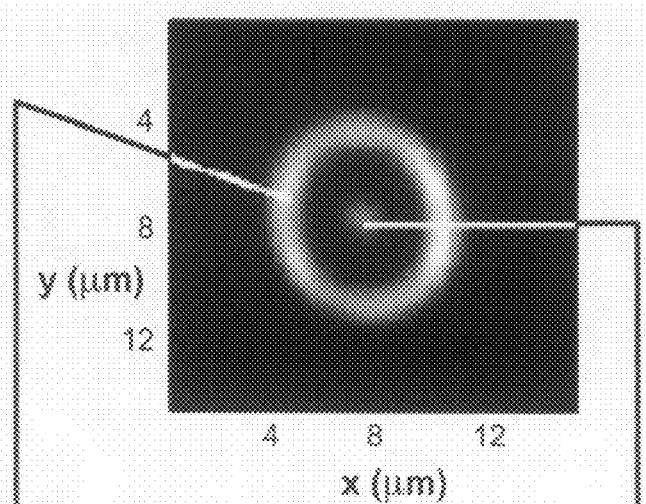
FIG. 1 illustrates a microscopic image of a 6 μm. polystyrene microsphere embedded in agarose gel, according to one embodiment.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are, references to the same embodiment; and such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

Without intent to limit the scope of the disclosure, exemplary instruments, apparatus, methods and their related results according to the embodiments of the present disclosure are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the disclosure so long as the disclosure is practiced according to the disclosure without regard for any particular theory or scheme of action.

Unless otherwise defined, all technical and scientific terms used herein have the same meaning as commonly understood by one of ordinary skill in the art to which this disclosure pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Embodiments of the present disclosure include systems and methods for identifying refractive-index fluctuations of a target, via partial wave spectroscopy, for example.

In one aspect, the present disclosure relates to optically examining a target object and identifying localized scattering signatures from an isolated single scattering element or a localized scattering element within a complex multi-particle system.

In this exemplary embodiment, an elastic backscattering spectroscopic microscope is provided according to the present disclosure, to identify localized scattering features arising from different parts of a single homogeneous micrometer-scale particle, including surface scattering (e.g., scattering due to the wave propagating on the sphere surface) and central scattering (e.g., scattering due to the wave traveling a round-trip optical path through the center of the particle). While the light emerging from a target of interest, for analysis is, in most cases, intended to be backscattered light, the principles of the present invention are contemplated as encompassing and being applicable to light that has been transmitted through the target of interest, and then sensed.

In one aspect, the present disclosure further relates to optically examining the target object to detect alterations in a cellular architecture at the nanoscale, for example, alterations of a single cell of a living subject. In addition, the ability to optically examine the target object at a scale of a single cell of a living subject can be applied to detection of carcinogenesis, for example, by optically examining a cytological sample.

In one aspect, embodiments of the present disclosure further comprise optically examining the AOM-treated rat model of colon carcinogenesis and observing an increase in the degree of disorder in cell architecture, for example, as indicated by fluctuations of the refractive-indices of the examined sample, at a nanoscale. In one embodiment, the cells exhibiting the increase in degree of disorder are histologically and/or cytologically normal. As such, note that via utilizing partial wave spectroscopy, carcinogenesis can be identified in histologically normal cells. In other embodiments, the cells may be histologically and/or cytologically abnormal.

The neoplastic disease is at least part of a process leading to a tumor or lesion, where the tumor or lesion can be abnormal cells or tissue (e.g., premalignant or cancerous), such as pancreatic cancer, a colon cancer, an adenomatous polyp of the colon, a liver cancer, a lung cancer, a breast cancer, and/or other cancers. While abnormal tissue can be a lesion or tumor, the abnormal tissue can also be tissue that precedes the development of dysplastic lesions that themselves do not yet exhibit dysplastic phenotype, and tissues in the vicinity of these lesions or pre-dysplastic tissues.

A particular application described herein is for detection of such pre-neoplastic changes in the colon in early colorectal cancer detection, in the pancreas for pancreatic cancer cells, in the buccal mucosa for lung cancer, other applications are described as well. Other biologically related applications include monitoring of bioengineered tissue development and/or cell growth. Yet other applications are contemplated beyond use of the disclosure in association with healthcare, such as characterization of polymer mechanical and molecular weight data, morphological structures of solid polymeric materials.

Elastic Backscattering

Light-scattering signals from microscale to nanoscale structures exhibit characteristic structure-dependent patterns in wavelengths (e.g., the spectrum) and scattering angles. The signatures, such as the spectrum and scattering angles, in the backward direction, are typically sensitive to subtle alterations in tissue architecture. Thus, in some instances, elastic light-scattering spectroscopy may be utilized for early diagnosis of carcinogenesis. In an elastic light-scattering spectroscopy experiment, a tissue area approximately several millimeters across is typically illuminated, for example, and the information on the average size of scatterers within this area is obtained.

In some applications, scattering signatures can be obtained from either an isolated single scatterer or a localized structure within a complex multi-particle system to determine the properties of the sample at a submicron scale, such as in the nanometer regime. For example, in cytological analyses, a few cancer cells can be identified and analyzed from a cell population via obtaining localized scattering signatures. Furthermore, characterization of scattering from a localized structure enables the origin of scattering signatures from biological cells, to identify cellular structures/organelles. Several techniques that incorporate the details of local microstructure with the scattering features include, for example, spectroscopic optical coherence tomography, spectral imaging, angle-dependent scattering, confocal spectroscopy, and micro-spectroscopy.

Thus, in accordance with one embodiment of this disclosure, elastic backscattering spectroscopic microscopy is operated to utilize both the diffraction-limited localized structural information provided by microscopy and the sub-diffractional sensitivity of spectral signatures. Thus, in one embodiment, the distinct and highly localized scattering features arising from different parts of a single homogeneous micrometer-scale particle, including surface scattering and central scattering, can be distinctly identified.

FIG. 1 illustrates a microscopic image of a 6 μm. polystyrene microsphere embedded in agarose gel, according to one embodiment.

Figure 2:
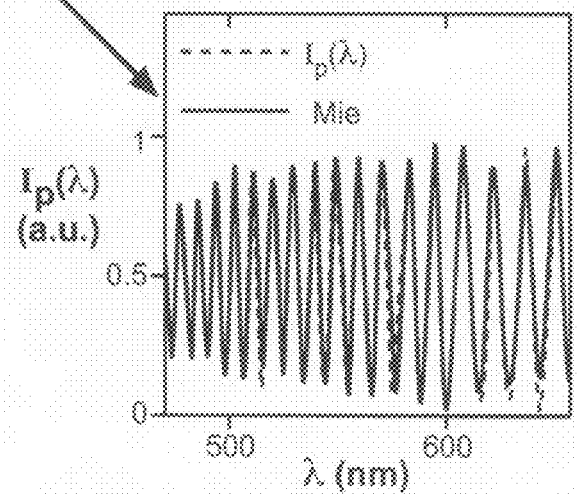
FIG. 2 illustrates the backscattering spectra recorded from the periphery of the polystyrene microsphere of FIG. 1 overlaid with a simulated scattering spectra computed from the Mie theory, according to one embodiment.
Figure 3:
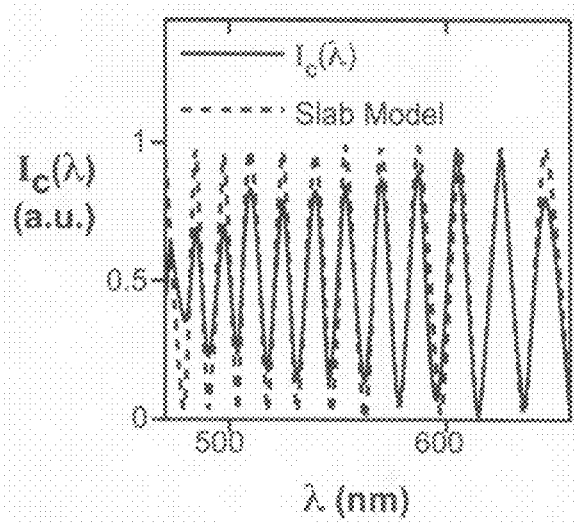
FIG. 3 illustrates the backscattering spectra recorded from light scattered from the center of the polystyrene microsphere of FIG. 1 overlaid with a simulated scattering spectra computed based on the slab model, according to one embodiment.

In this example, the agarose gel concentration is approximately 1% having a microsphere density of ~8×105 particles/ml. As shown in the image, there are two visible bright areas: in the periphery of the sphere and in its center. Similar patterns having two visible bright areas can be observed for microspheres with other sizes (D=3.1, 4.78, 10.1 μm). The scattering spectra from the periphery [Ip($\lambda$)] and the center [Ic($\lambda$)] of the microsphere are shown in FIG. 2 and FIG. 3, respectively. In this example, I($\lambda$) is the backscattered spectrum normalized by the spectral profile of the incident light source. The spectra exhibit the high-frequency oscillations known as the ripple structure characteristic of scattering by micrometer-sized particles. Since the high-frequency component of the spectrum is to be analyzed, in one embodiment, the low-frequency components can be removed with a high-pass filter.

FIG. 2 illustrates the backscattering spectra recorded from the periphery of the polystyrene microsphere of FIG. 1 overlaid with a simulated scattering spectra computed from the Mie theory, according to one embodiment.

In one embodiment, the spectral feature of periphery intensity Ip($\lambda$) is recorded and examined. The ripple structure as shown in the figure arises from the interference effect between the waves propagating on the surface (e.g., the surface wave) and can be modeled by far-field Mie theory. Mie theory describes the Mie scattering of electromagnetic radiation by spherical particles via an analytical solution of Maxwell's equations. In most instances, the Mie theory is applicable for spherical particles having an extensive range of the ratio of the diameter of spherical particles to the wavelength of electromagnetic radiation. The reference to particles in the context of the Mie theory usually refers to an aggregation of material having a refractive index that is different from the refractive index of the surrounding material.

As shown in the figure, there is a good correlation between Ip($\lambda$) and the spectrum determined by the Mie theory, indicating that far-field Mie scattering is dominated by surface scattering, in agreement with theoretical explanation.

Partial Wave Spectroscopy

FIG. 3 illustrates the backscattering spectra recorded from light scattered from the center of the polystyrene microsphere of FIG. 1 overlaid with a simulated scattering spectra computed based on the slab model, according to one embodiment.

In one embodiment, the intensity of the spectra of the light scattered from the center of the microspheres can be recorded. The light scattered from the center of microspheres corresponds to light waves that reflect between intracellular structures, along a 1D trajectory, for example. As can be seen, the ripple in the intensity plot of light backscattered from the center oscillates slower than one from the periphery as illustrated in FIG. 2. The slower oscillating ripple is not what is predicted based on modeling with the far-field Mie theory. Furthermore, the anomalous ripple structure Ic($\lambda$) is observed to be independent of the refractive indices of the surrounding media (data not shown), whereas Mie theory predicts that the ripple structure depends on the relative refractive index between the scatterer and the medium.

The slower oscillation pattern of the light scattered from the center of the microsphere may be due to the interference between the light reflected from the sphere-medium interface and that traveling a round-trip optical path through the center of the sphere. Thus, the frequency and peak positions of the backscattered spectrum can be predicted from a uniform slab model Is($\lambda$) having a thickness substantially equivalent to the sphere diameter. The 1D slab model is a simplified model for computing the spectra of backscattering from a slab with a refractive index that varies in one direction (e.g., n(z)). The backscattering spectra computed from the 1D slab model Is($\lambda$) can in most instances be determined analytically. As shown in the figure, the spectral peaks of the backscattered spectrum as determined by the uniform slab model Is($\lambda$) correspond to the spectral peaks of Ic($\lambda$). Thus, the uniform slab model can be used to model partial wave spectroscopy signals recorded from backscattered light of a sample of interest.

Further, a number of microspheres (N=30) with different refractive indices (n=1.59, 1.46) and various diameters D from 1.5 to 6 μm (data not shown) were also imaged. The spectra of the backscattered light from the microspheres were obtained and determined to be a good fit compared with the spectra obtained by simulation of the slab model.

Figure 4:
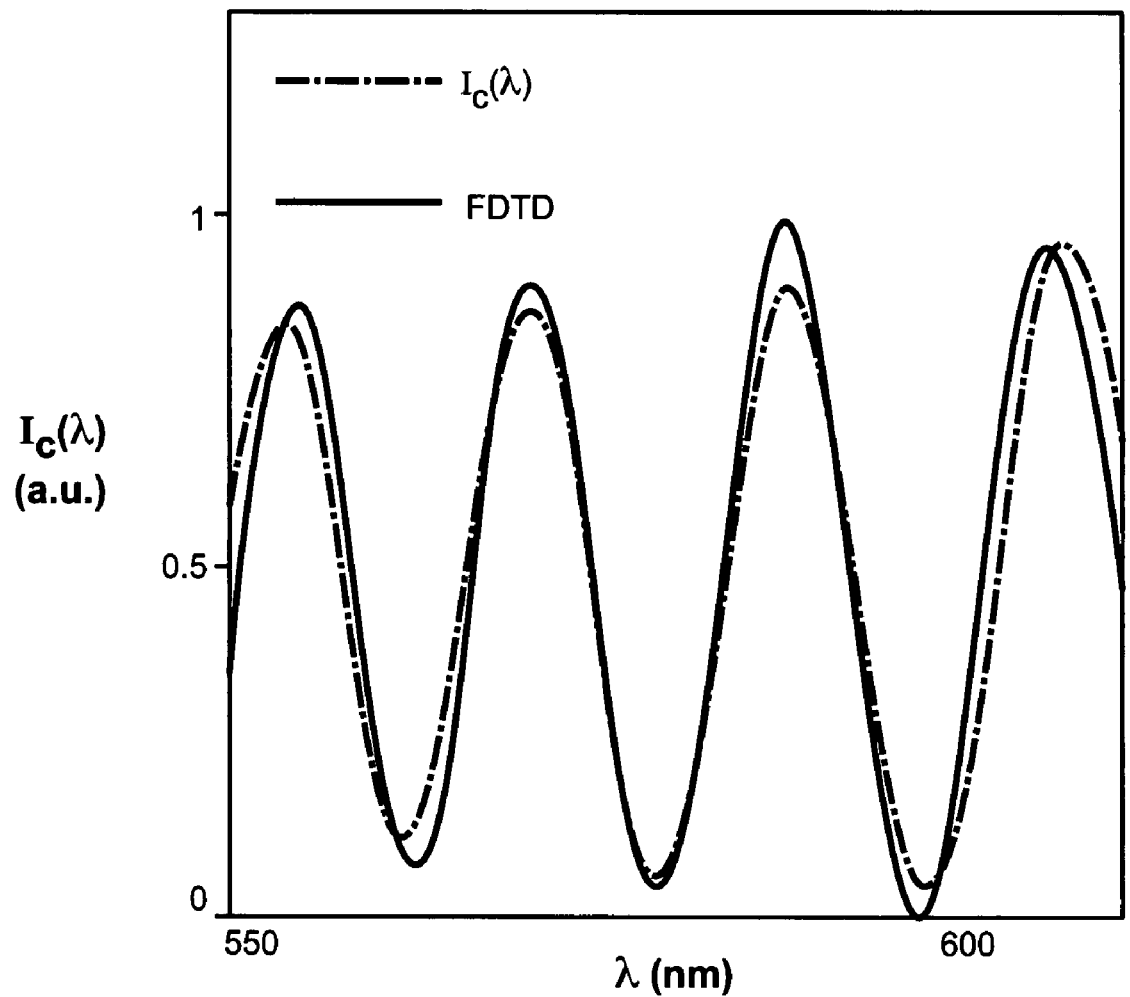
FIG. 4 illustrates the backscattering spectra recorded from the center of the polystyrene microsphere of FIG. 1 overlaid with a scattering spectra computed from FDTD simulations, according to one embodiment.

FIG. 4 illustrates the backscattering spectra recorded from the center of the polystyrene microsphere of FIG. 1 overlaid with a scattering spectra computed from the finite-difference time-domain (FDTD) simulations, according to one embodiment.

In one embodiment, recording the backscattered spectra Ic($\lambda$) and fitting Ic($\lambda$) to the spectra computed from the slab model or by the finite-difference time-domain (FDTD) method can be used to characterize the size of the particle with sub-diffractional accuracy. For example, the accuracy with which the particle size can be determined from the scattering spectra can be determined by comparing the recorded spectra with numerical data generated by the finite-difference time-domain (FDTD) method.

In the finite-difference time-domain (FDTD) method, a space-time mesh is introduced and Maxwell's equations can be replaced by a system of finite-difference equations on the mesh. Thus, via FDTD simulations, scattering intensities can be determined at arbitrary spatial locations for pre-determined geometries and boundary conditions by solving the Maxwell's equations numerically. In the simulations performed in this experiment, the geometry of dielectric microspheres of various sizes is incorporated into the FDTD grid using a staircasing scheme with spatial resolution of 12.5 nm.

In one embodiment, the scattered-field technique can be employed to source a time-domain pulsed plane wave that accommodates the complete frequency range of visible light. In one embodiment, the center-scattering spectrum, Ic($\lambda$), can be obtained by performing a discrete Fourier transform of the time domain field intensity at an observation point located on the optical path through the center of the microsphere and normalized by the source spectrum. The numerical simulation can be validated by comparing the simulations with experimental results for a microsphere with D=6 μm. As shown in the figure, the spectrum computed with FDTD simulation accurately predicts the backscattered spectrum Ic(λ) recorded experimentally.

Figure 5:
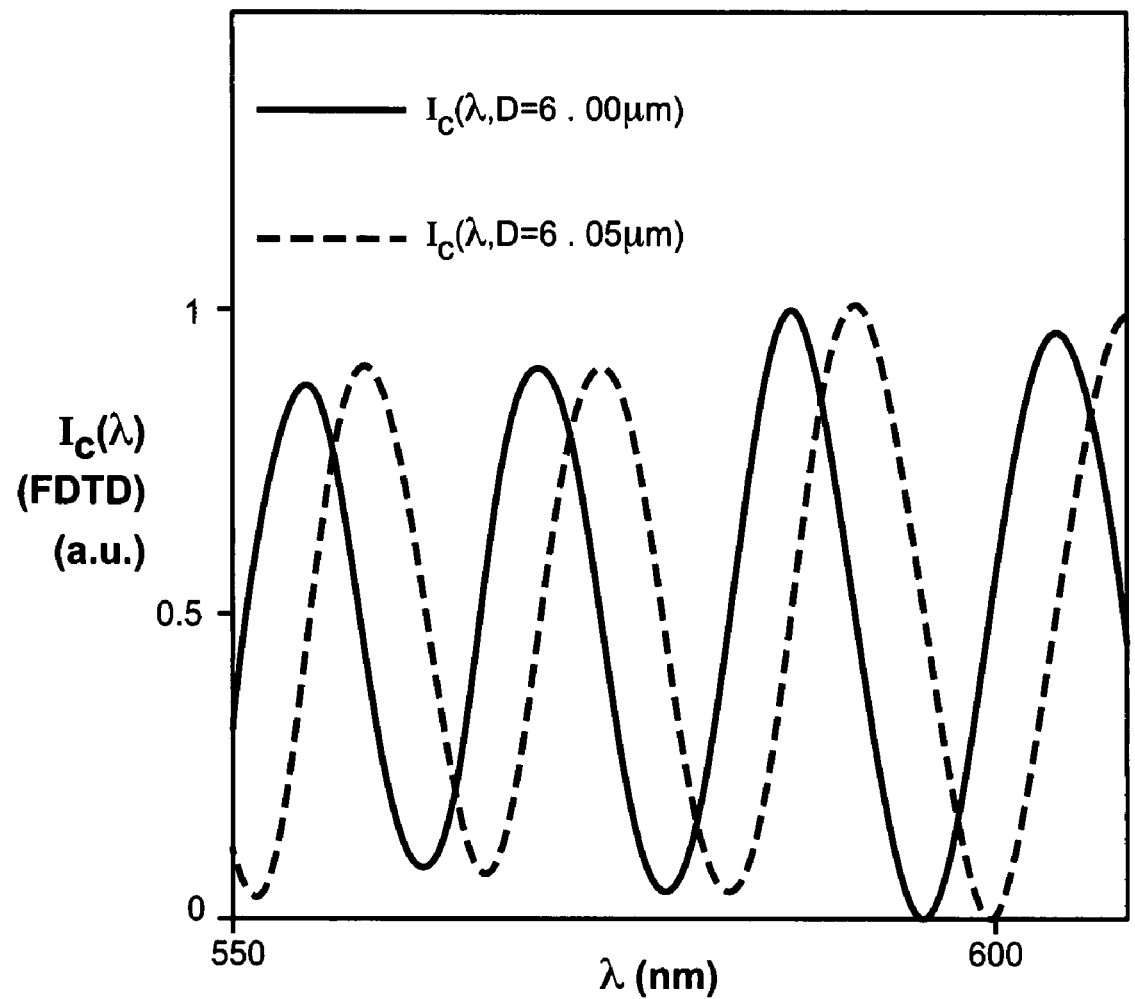
FIG. 5 illustrates the backscattering spectra computed based on FDTD simulations for two spheres with differing sizes in diameter, according to one embodiment.

FIG. 5 illustrates the backscattering spectra computed based on FDTD simulations for two spheres with differing sizes in diameter, according to one embodiment.

The recorded spectra from spheres can be used to determine the size of the diameter, in one embodiment. For example, the size of the microsphere in the FDTD model can be varied to test the sensitivity of the dependence of the backscattered spectra Ic(λ) on particle size. FIG. 5 shows that FDTD-calculated spectra Ic(λ) is observably different for microspheres with 50 nm. difference in diameter. Furthermore, the peak position of the backscattered spectra Ic(λ) for a sphere can be fitted well by the slab model with the same refractive index and a thickness equivalent to the sphere diameter, in one embodiment. Thus, particles with different sizes can be identified with sub-diffractional nanoscale accuracy via curve fitting recorded backscattered spectra to the spectra determined by the slab model, for particles of different sizes, according to one embodiment. In some instances the spectra can be determined by FDTD.

Figure 6:
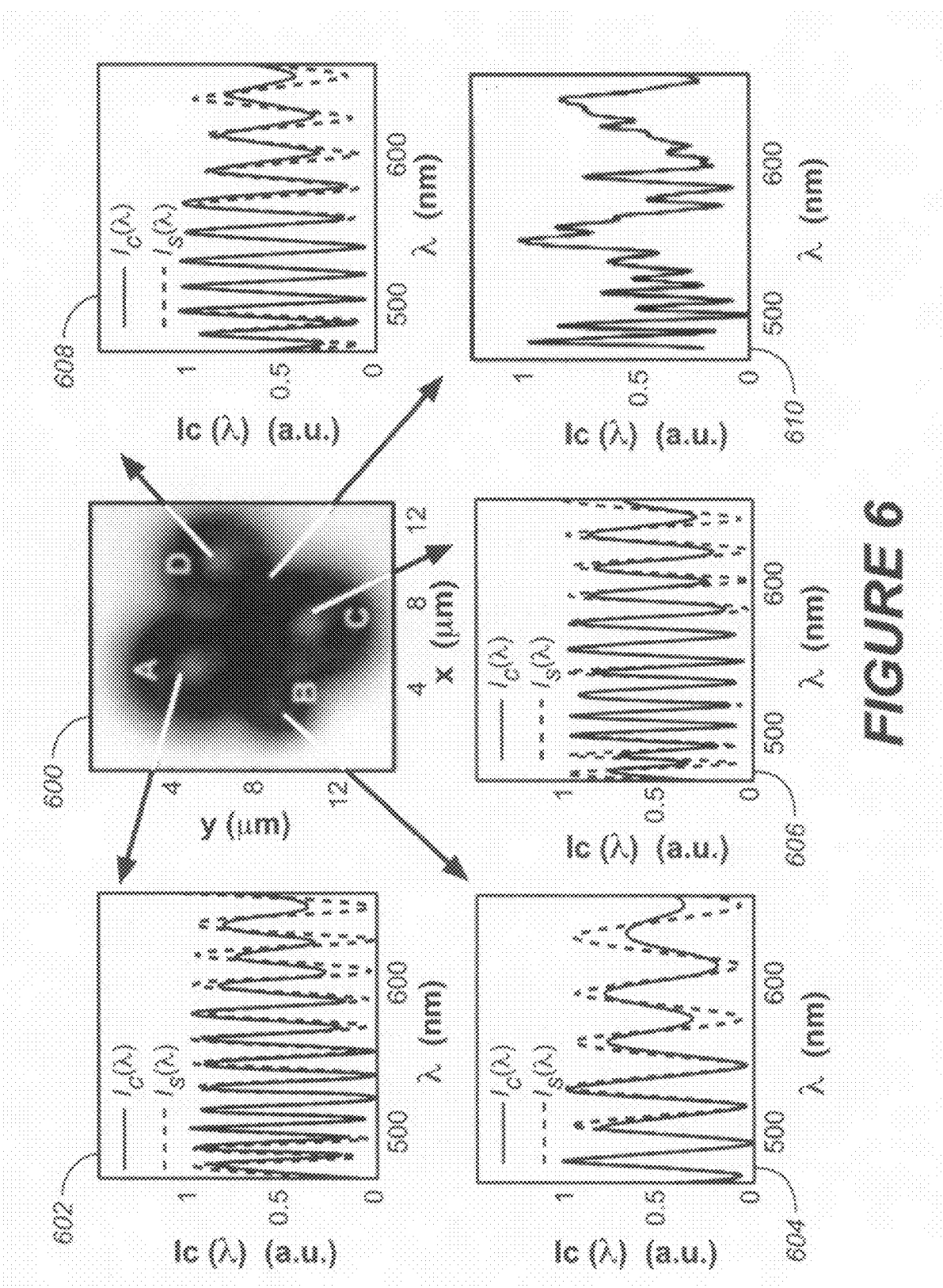
FIG. 6 illustrates an image of aggregated polystyrene microspheres in air with varying mean diameters, and the scattering spectra $Ic(\lambda)$ recorded from the center each of the four microspheres fitted to the scattering spectra derived from the slab model $Is(\lambda)$, according to one embodiment.

FIG. 6 illustrates an image of aggregated polystyrene microspheres in air with varying mean diameters, and the scattering spectra Ic(λ) recorded from the center each of the four microspheres fitted to the scattering spectra derived from the slab model Is(λ), according to one embodiment.

Localized scattering signatures within a complex system can be identified by analyzing the backscattered spectra Ic(λ), according to one embodiment. For example, aggregated polystyrene microspheres with different sizes can be used, as shown in FIG. 6. In plots 602, 604, 606, 608, even though the particles are densely packed, individual single scattering features Ic(λ) can be discerned without being affected by the multiple scattering between particles.

In one embodiment, the size of the particles comprising the aggregated complex can be differentiated via fitting the recorded backscattered spectra with the a predetermined spectra. In one embodiment, the predetermined spectra is computed from the slab model. For example, the particle sizes can be accurately obtained with a standard error ~50 nm. by fitting the spectra predicted by the slab model Is(λ) to the backscattered spectra Ic(λ) by using a least squares minimization algorithm. In addition, the backscattering spectra Ic(λ) is independent of the refractive index of the surrounding medium (data not shown), which facilitates the detection of scattering signatures from a single particle. In comparison, the surface scattering in plot 610 is affected by the refractive index of the medium and multiple scattering interactions between neighboring particles.

Thus, partial wave spectroscopy enables detection of localized scattering features within a single scattering particle and densely packed scatterers. In some embodiments, partial wave spectroscopy can be used to characterize internal structures of living, fixed, and/or stained cells (e.g., as part of a cytological preparation), for identification of spectroscopic markers associated with disease-specific cellular changes. Partial wave spectroscopy may further facilitate the determination of the origin of light scattering signals and image formation in several modalities of optical microscopy and spectroscopic optical coherence tomography. Partial Wave Spectroscopy virtually divides a target into the collection of parallel channels each with the diffraction-limited transverse size, detects backscattered waves propagating within these channels, and quantifies the statistical properties of the refractive index fluctuations within a target by the spectroscopic analysis of the fluctuating part of the backscattering spectrum in the far-field.

Further, in one embodiment, partial wave spectroscopy can be used to probe tissue architecture. For example, spatial fluctuations of tissue refractive index can be identified by partial wave spectroscopy to further provide indication of the spatial variation of the concentration of intracellular solids (e.g., proteins, DNA, and RNA). In particular, when photons propagate in one-dimension, the reflected signal in 1D is non-self averaging in length scales for weak refractive index fluctuations. Therefore, due to the interference of light waves traveling along 1D trajectories, the backscattered light can reflect refractive index fluctuations thus enabling characterization of cell architecture, for example, on a nanoscale.

To evaluate tissue or cell architecture, for example, the backscattered light intensity as a function of wavelength is recorded and analyzed. Optical markers and statistical parameters of the optical markers can be determined from the backscattered light spectra towards evaluating tissue/cell architecture. An exemplary set of optical markers and statistical parameters are described here, yet other optical markers and statistical parameters not specifically described are contemplated and fall within the scope of the disclosure.

Reflection Coefficient R(k)

The spectrum of the fluctuating part of the reflection coefficient R(k) can be determined from the backscattering spectrum I(k) for each portion of the acquired image.

To determine R(k), the high-frequency noise of the backscattering spectrum I(k) can initially be filtered out utilizing a low-pass filter. The high-frequency noise, in one aspect, arises from signal characteristics devoid of information regarding the disorder (e.g., as indicated by the fluctuation of the refractive index) of the sample at a sub-micron scale, which can be obtained, for example, via analytically computing the noise level of the light backscattered from a sample of polystyrene microspheres with no disorder. Thus, for example, the amplitude of the noise and the cut off frequency can be determined from computations of backscattered light of the polystyrene sample. In one instance, a 6th order low-pass Butterworth filter with a cut off frequency of approximately 0.08 can be used.

The cutoff frequency of the low pass filtered to be used may additionally correspond to the spectral resolution of the instrumentation. Since spectral fluctuations with spectral frequencies higher than that of the point spread function of the instrument, is attributed to the instrument noise, the filter can be designed to filter out these fluctuations, to obtain a noise-filtered spectra I'(k). For example, if the point spread function-limited spectral resolution of the instrument has a bandwidth of 3 nm, the CCD can over sample a spectrum with, for example, a bandwidth of 0.25 nm.

A polynomial function <I(k)> can be chosen to fit I'(k), the order of the polynomial can be determined as suitable to match the slow varying part of I'(k), for example a fourth-order polynomial. According to one embodiment, R'(k) can be determined by the equation $R'(k)=[I'(k)-<I(k)>]/I_o(k)$, where $I_o(k)$ is the intensity of the incident light. <I(k)> is the low-pass filtered intensity spectrum, which does not have the high-frequency spectral component to be analyzed to determine the disorder strength, $L_d$.

The minimal value of R'(k) can be shifted to zero to obtain a positive spectra. Thus the fluctuating part of the reflection coefficient R(k) can be expressed as $R(k)=R'(k)+|R'(k)|_{min}$. In one embodiment, determining the fluctuating reflection coefficient R(k) identifies the fluctuating component of the backscattering spectra that arises from reflected intensity after multiple interference of photons from refractive index fluctuations (e.g., fluctuations at a nanoscale) in a scattering medium, such as a cell.

Disorder Strength $L_d$

The disorder strength $L_d$, is defined as $L_d=\alpha<\Delta n^2>l_c$, where $<\Delta n2>$ is the variance of refractive index fluctuations in a single 1D channel, $l_c$ is the spatial correlation length of these refractive index fluctuations, and $\alpha$ is a numerical factor. Thus, the disorder strength $L_d$, is proportional to both the refractive index fluctuations and the correlation length.

According to the mesoscopic light transport theory, which describes light scattering for a regime between a single scatterer and multiple scatterers, the disorder strength $L_d$ can be determined by two experimentally acquired physical quantities: the wave-number-dependent reflection coefficient R(k), and the autocorrelation function $C(\Delta k)=\langle R(k)R(k+\Delta k)\rangle/\langle R(k)R(k)\rangle$ of the reflection coefficient, where k is the wavenumber, in one embodiment.

In a weakly disordered medium (e.g., R(k)<<1) of length L, the distribution of R(k) over 1D channels, according to the mesoscopic light transport theory, follows a log-normal distribution with the mean of the reflection coefficient, $<R>\cong½ \exp(4 k2 L_dL/n_0^2-1)$, where $n^0$ is the mean refractive index. Given that in a cell, $l_c$ is typically on the order of the nanometer scale and the variance of refractive index fluctuations is much smaller than 1, (e.g., $L_d$<<1), the expression for the mean of the reflection coefficient can be further simplified as:

$$<R>\cong 2k2L_dL/n_0^2, \quad (1)$$

Thus, in a biological cell, according to equation (1), R(k) is typically expected to be proportional to the disorder strength $L_d$, in accordance with one embodiment. Furthermore, $C(\Delta k)$ can be expressed as:

$$C(\Delta k)\cong\exp[-(\Delta k)^2 n_0^2 L/2k^2 L_d](\text{or, }\ln(C(\Delta k))\propto -(\Delta k)^2 n_0^2 L/2k^2 L_d)) \quad (2)$$

Thus, in one embodiment, the disorder strength $L_d$ can therefore be calculated from the above two equations (1) and (2).

The dependence of the disorder strength Ld on nanoscale refractive index fluctuations has been demonstrated via numerical experiments. Since $L_d$ reflects the spatial fluctuations of the refractive index and since the refractive index is proportional to the concentration of intracellular molecules, the disorder strength reflects the spatial variation of intracellular material, for example, at the sub-micron or nanoscale level. At a particular location in a cell, the standard deviation of the refractive index $\Delta n$ may be proportional to the local concentration of intracellular solids.

Numerical computations have determined that $L_d\propto<\Delta n^2>l_c$, for $l_c$ in the nanometer range (e.g., ranging from 1 to 65 nm. or length scales considerably below the diffraction limit), and for $\Delta n$ ranging from 0.01 to 0.05 (e.g., in the biologically relevant regime). Since $L_d$ is linearly dependent on $l_c$ for $kl_c$<<1, in principle, there is no limitation on the minimum correlation length that can be assessed by means of spectral analyses of 1D-propagating photons.

Correlation Length of Refractive Index $l_c$

Figure 13:
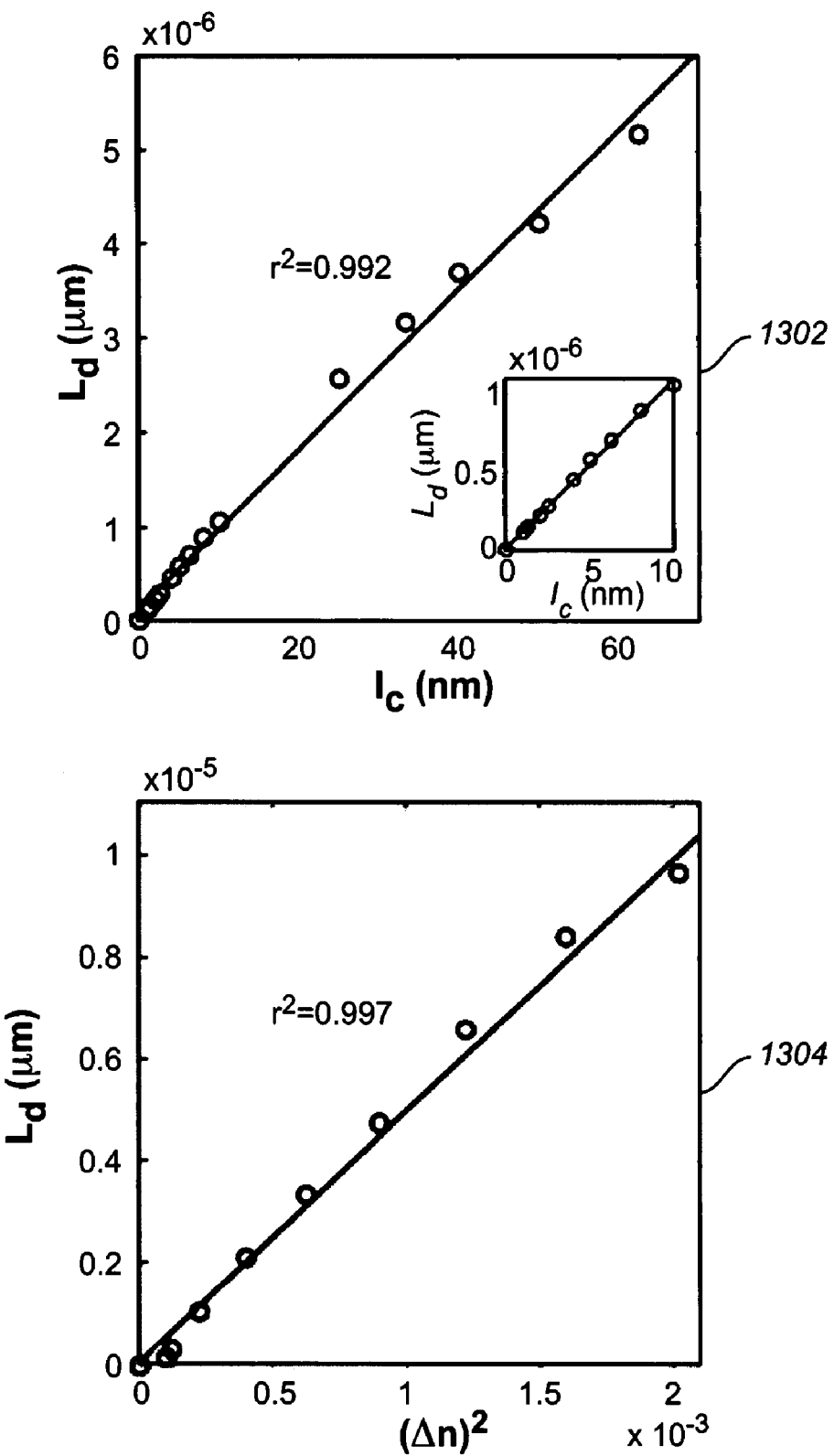
FIG. 13 illustrates plots showing the variation of the disorder strength Ld with the correlation length $l_c$ and refractive index fluctuations $<\Delta n2>$, as determined by the 1D slab model, according to one embodiment.

The correlation length of the refractive index $l_c$ can be described by the equation: $<\Delta n(L)\Delta n(L')>\cong<\Delta n^2>\exp[-|L-L'|/l_c]$ where the correlation length $l_c$ is typically in the nanometer range (e.g., from 1 to 65 nm and $kl_c$<<1 where k is the wave number). The disorder strength $L_d$ can be determined from Equations (1)-(2). The spatial correlation length of refractive index fluctuations $l_c$ can be interpreted as corresponding to the size of the macromolecular "building blocks" of the cell. FIG. 13 shows that $L_d$ is linearly dependent on both $l_c$ and $<\Delta n2>$. As shown in the figure, the disorder strength is proportional to the nanoscale correlation length at scales much less than the diffraction limit.

Figure 7:
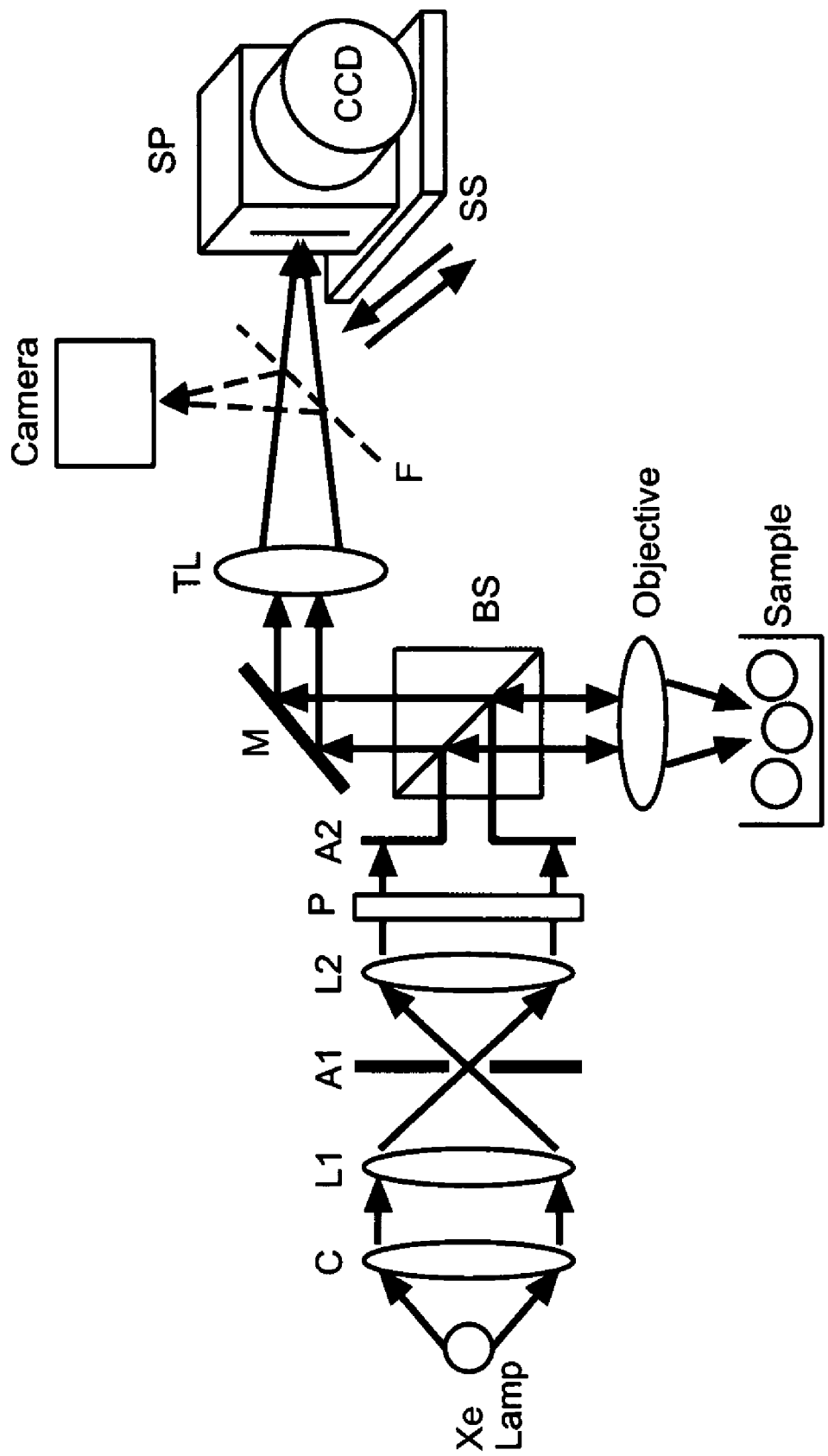
FIG. 7 illustrates an exemplary schematic of the spectroscopic system for performing partial wave spectroscopy, according to one embodiment.

FIG. 7 illustrates an exemplary schematic of the spectroscopic system for performing partial wave spectroscopy, according to one embodiment.

The system to illuminate light on a target, includes, in one embodiment, a light source to provide incident light having at least one spectral component. The light source may be a white light source. In addition, the light source may obtain the at least one spectral component of light from a plurality of narrowband light sources, and/or one or more of an arc-lamp, a white light emitting diode, a laser source, and a color light emitting diode. The laser source may include one or more lasers with one or more wavelengths of emission. In one embodiment, the color light emitting diode comprises one or more light emitting diodes with one or more spectral emission ranges.

In one embodiment, the system further includes a first set of one or more optical components operatively configured to collimate the incident light and/or a second set of one or more optical components operatively configured to focus the incident light on the target. The first set of one or more optical components may include a 4f system and an aperture wherein the 4f system is a two lens 4f system, for example. The lens may be a positive lens and/or one or more of a Fourier lens, a ball lens, a graded refractive index lens, an aspheric lens, cylindrical lens, convex-convex lens, and plano-convex lens. Furthermore, the aperture may be disposed in a common focal plane of the two lenses. In one embodiment, the system further includes a condenser disposed between the light source and the 4f system. The second set of the one or more optical components may further include an objective lens, where the backscattered light is collected by the objective lens. The system may further include a tube lens to focus the backscattered light collected by the objective lens to magnify the image of the backscattered light and/or a flipper mirror operatively configured to deflect the backscattered light collected by the objective lens. In one embodiment, the flipper mirror can be operatively configured to deflect the backscattered light to a camera to visualize an image before it is recorded.

The system may also include a receiving end to record the intensity of one or more preselected spectra of backscattered (or through-transmitted) light. A spectrum corresponds to a preselected portion of the backscattered (or through-transmitted) light emerging from a preselected portion of the target, which may correspond to backscattered/through-transmitted light propagating, along a single dimension of travel, within a "channel" within a target. The backscattered light can be backscattered from illumination of the incident light on an illuminated portion of the target. The receiving end may also include an imaging spectrograph and/or a light detector to record an image of the backscattered light from the target. In one embodiment, the receiving end includes a light detector coupled with the imaging spectrograph, and a scanning stage coupled with the image spectrograph and the light detector. The scanning stage can be operatively configured to move about a predetermined position. The light detector may be a CCD camera and/or a plurality of photodetectors. In yet another embodiment, the receiving end further may include one or more single channel linear-array spectrometers and/or filters to record an intensity of one or more of at least one spectral component of backscattered light. The filter may be one or more of a tunable filter, a filter wheel, and dichronics.

In the example embodiment illustrated in FIG. 7, the broadband white light from a Xe lamp (e.g., 100 W) can be collimated by a 4f system (L1-A1-L2) with full divergence angle of approximately ~0.80. The collimated light can be focused onto a sample by a low numerical-aperture (NA) objective (e.g., NA=0.4). In one embodiment, the diameter of a beam of light illuminated on the target is substantially larger than a size of the target such that the beam of light illuminated on the target corresponds to a plane wave. In this example, the beam diameter is approximately 120 μm. The backscattered light can be collected by the same objective and focused by a tube lens to form a magnified image. In one embodiment, the imaging spectrograph coupled with the CCD camera can be mounted on a scanning stage. In addition, the flipper mirror can be directed the image onto a digital camera for visualization of the image for adjusting the distance between the objective lens and the sample, according to one embodiment.

Figure 8:
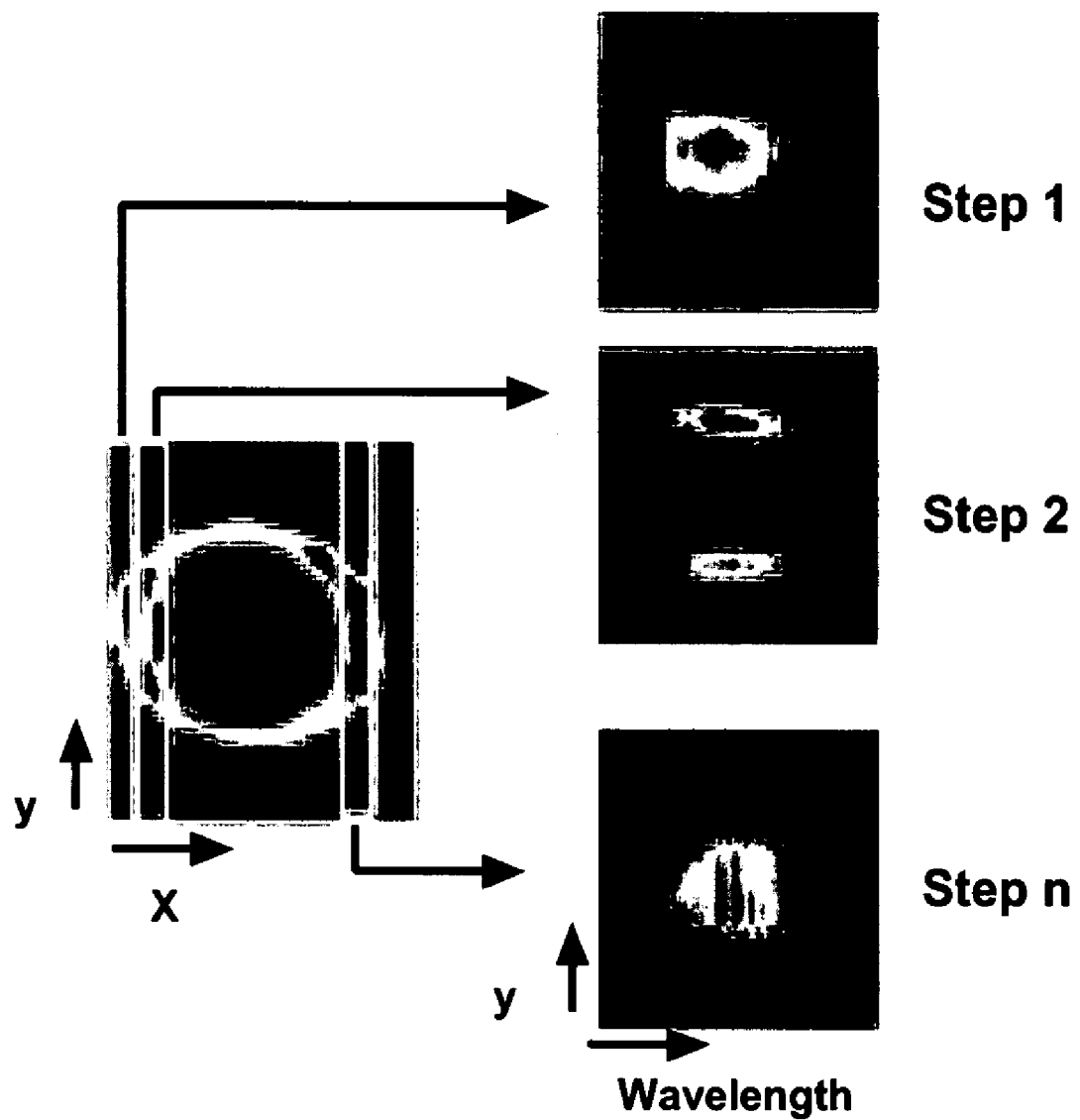
FIG. 8 illustrates an exemplary image and exemplary spectra of a microsphere acquired via partial wave spectroscopy by the spectroscopic system, according to one embodiment.

FIG. 8 illustrates an exemplary image and exemplary spectra of a microsphere acquired via partial wave spectroscopy by the spectroscopic system, according to one embodiment.

To obtain an image and spectra, the entrance slit of the imaging spectrograph can, for example, be scanned along the x axis of the image plane with a predetermined step size (e.g., 10 μm.), in one embodiment. In a scanning step, the CCD camera can record a matrix with its y axis corresponding to a spatial position along the y axis of the image and x axis corresponding to the wavelength of light. Thus the instrument can record the image with diffraction-limited spatial resolution by integrating the intensities of different wavelengths from the CCD. For a pixel of the final image there is a corresponding spectrum that is recorded, in one embodiment, to provide a sub-diffractional sensitivity (e.g., in the nanometer scale) for characterizing the structure of the scatterers even despite the fact that the size of the preselected portion of the target itself may be diffraction limited.

Human Cancer Cell Line Model

In one embodiment, partial wave spectroscopy can be used to identify architectural changes (e.g., on the sub-micron, nanoscale) in cells that are otherwise histologically indistinguishable, such as HT29 human colon cancer cell lines. Since the malignant behavior of the HT29 cells can be controlled by genetic modification, in one embodiment, different genetic variations of HT29 cells can be optically examined by partial wave spectroscopy for determining whether the difference in malignant behavior can be optically identified. Three variants of HT29 cells are used in this example: original HT29 control cell line; HT29 cells after knockdown of a tumor suppressor gene, C-terminus Src kinase (CSK), which leads to increased aggressiveness and malignant behavior, and HT29 cells after knockdown of the epidermal growth factor receptor (EGFR) gene, which suppresses the malignant aggressiveness of the cell line.

Despite differences in malignant behavior, these variants of HT29 do not exhibit histological differences observable either by microscopic examination of living cells or stained cytological preparations. In this example, the three types of HT29 cells are fixed in ethanol at the same time point to make sure that the cells experience the same growth time after genetic treatment and that no further growth occurred within the time of the experiment. Cytopathology was performed on each variant of HT29 cells by an expert cytologist confirming that the three lines are cytologically indistinguishable. Partial wave spectroscopy measurements were conducted on ~30 randomly selected cells from each of the three cell types (e.g., ~500 1D channels per cell).

In one embodiment, partial wave spectroscopy instrument can measure the backscattering signal $I(\lambda, x, y)$ for a point (x, y). The fluctuating component of the backscattered signal $R(\lambda, x, y)$ can then be extracted from $I(\lambda, x, y)$, in one embodiment, by filtering out the noise in $I(\lambda)$, subtracting out the non-fluctuating component $I_0(\lambda)$, and shifting the residual by a constant factor, such that $R(\lambda)$ varies from zero to a finite number. The parameters of the signal analysis can be optimized in numerical experiments with simulated and experimental data, on a case by case basis.

Figure 9A:
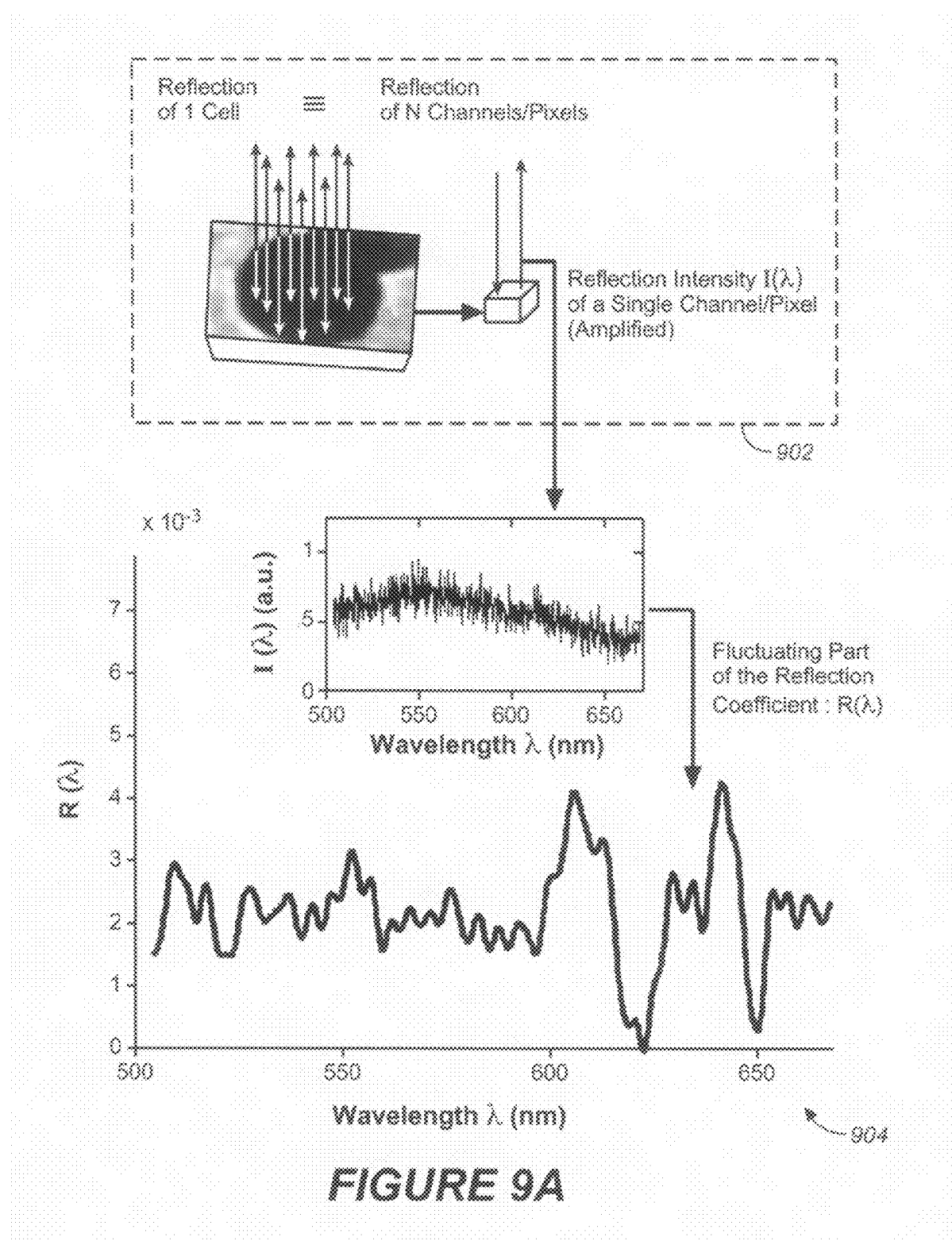
FIG. 9A illustrates an image of a cell acquired via partial wave spectroscopy and a plot of the reflection coefficient spectra $R(\lambda)$ after noise removal and background reflection, according to one embodiment.

FIG. 9A illustrates an image of a cell acquired via partial wave spectroscopy and a plot of the reflection coefficient spectra $R(\lambda)$ after noise removal and background reflection, according to one embodiment.

Plot 902 is a microscopic image of a HT29 cell obtained via partial wave spectroscopy. As shown in plot 904, the reflection coefficient spectra $R(\lambda)$ is the fine fluctuating component of the backscattering spectrum $I(\lambda)$ that originates from the interference of 1D-propagating photons reflected from nanostructural refractive index fluctuations in the colonic cell. The inset of plot 904 is a plot of the backscattering spectrum $I(\lambda)$ from a preselected portion of a HT29 cell recorded with partial wave spectroscopy.

Figure 9B:
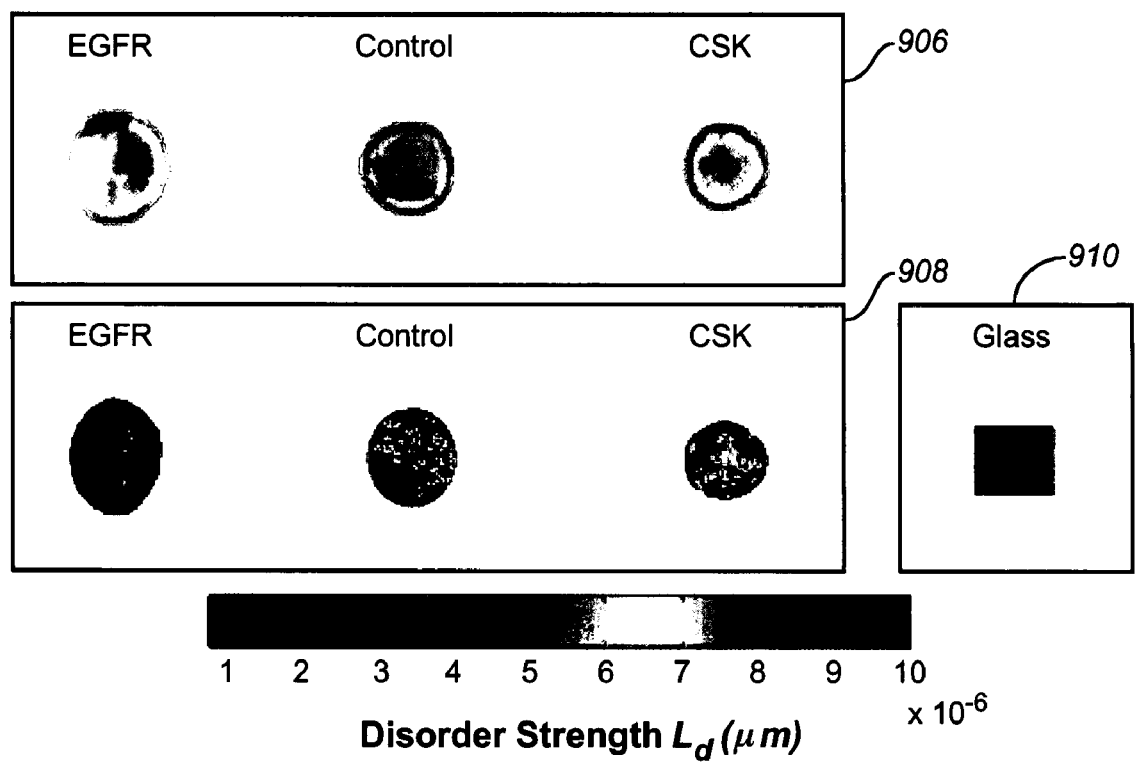
FIG. 9B illustrates a set of cytological cell images and a set partial wave spectroscopy cell images, obtained for EGFT knockdown HT29 cells, normal HT29 cells, and CSK knockdown HT29 cells, according to one embodiment.

FIG. 9B illustrates a set of cytological cell images and a set partial wave spectroscopy cell images, obtained for EGFT knockdown HT29 cells, normal HT29 cells, and CSK knockdown HT29 cells, according to one embodiment.

The set of images 906 illustrates the cytological cell images obtained via Hemotoxylin and Eosin staining of the three cell types. As can be seen, the cytology images look substantially similar and indistinguishable for EGFT knockdown HT29 cells, normal HT29 cells, and CSK knockdown HT29 cells. The set of images 908 represent in color, the variation in disorder strength in the imaged cell determined from partial wave spectroscopy. The increase of the disorder strength and the standard deviation of the disorder strength can be observed for the CKS knockdown HT29 cells relative to the control HT29 cell, and the decrease of the disorder strength and the standard deviation of the disorder strength of the EGFR knockdown HT29 cells relative to the control HT29 cell. Thus, a cell from the most aggressive cell line (CSK-knockdown) has the highest intracellular disorder strength, while the least aggressive cell line (EGFR-knockdown) exhibits the least disorder. Thus in one embodiment, identifying higher disorder strength is associated with determining increased malignant behavior in cells.

To determine the noise level of performing partial wave spectroscopy, the disorder strength of the glass slide covering the cells for which partial wave spectroscopy is performed on. As shown in image 910, the disorder strength of glass slide is uniformly much smaller than that relative to the EGFR knockdown HT29 cells, and thus negligible.

Figure 9C:
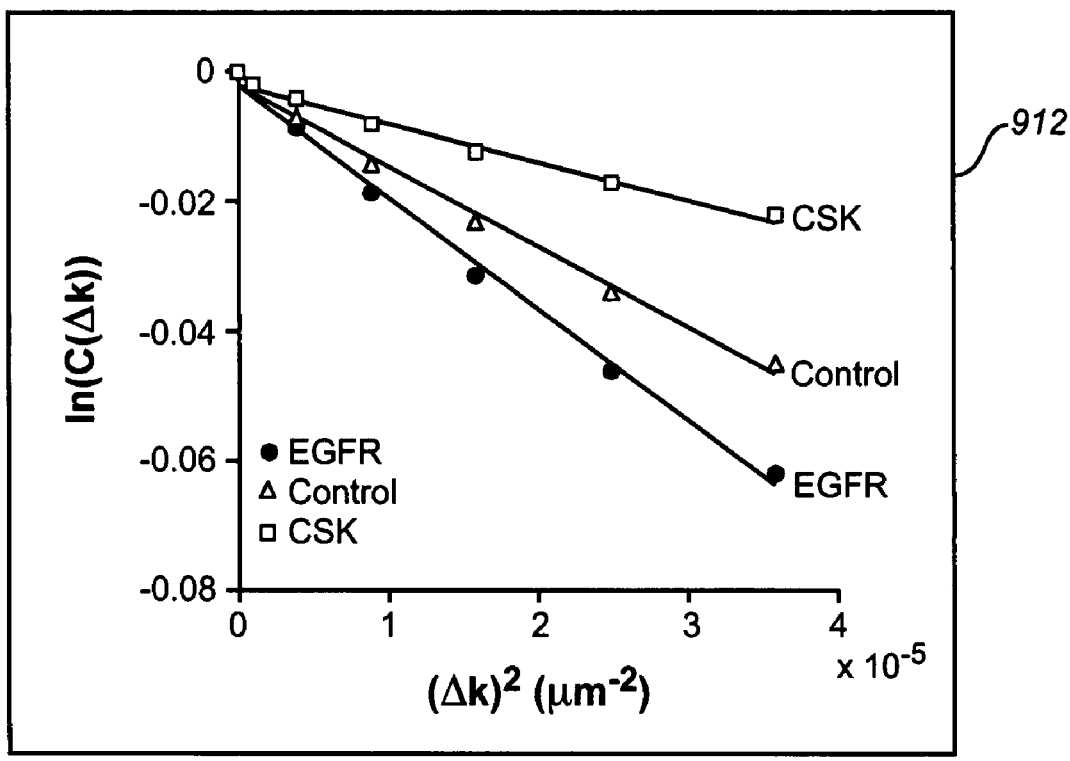
FIG. 9C illustrates plots of statistical parameters of the reflection coefficient $R(k)$ and the disorder strength Ld for EGFR HT29 cells, control HT29 cells, and CSK HT29 cells, according to one embodiment.
Figure 9C:
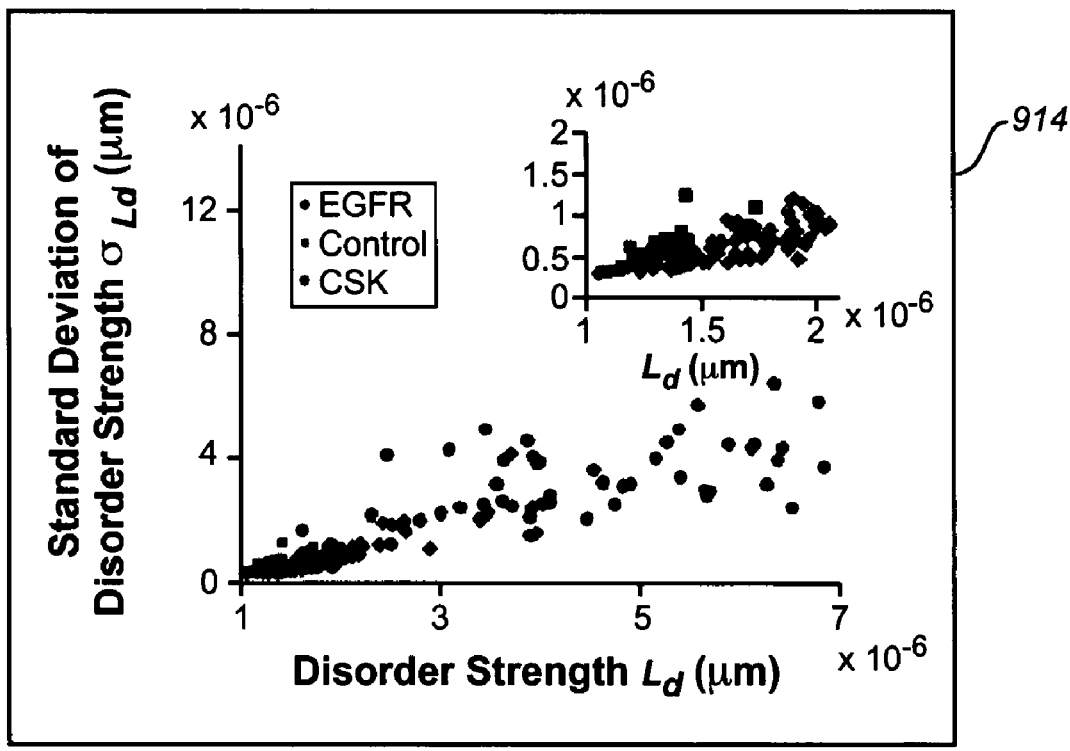

FIG. 9C illustrates plots of statistical parameters of the reflection coefficient $R(k)$ and the disorder strength Ld for EGFR HT29 cells, control HT29 cells, and CSK HT29 cells, according to one embodiment.

Plot 912 illustrates the decay of the autocorrelation function of the reflection coefficient $R(k)$ for the three types of HT29 cells. As shown in the figure, the decay rate of the autocorrelation function $\ln(C(\Delta k))$ vs. $(\Delta k)^2$ is faster for the EGFR knockdown HT29 cells and slower for the CSK knockdown HT29 cells relative to the control cells.

A number of statistics of $L_d$-distributions can be determined from the disorder strength images. For example, a cell can be characterized by a set of two convenient statistics: the mean intracellular disorder strength, $L_{d_c}$, (e.g., the average $L_d(x, y)$ over x and y) and the intracellular standard deviation $\sigma_c$. The averages of the cell means $\langle L_{d_c}\rangle$ and $\langle \sigma_c \rangle$ for a group of cells (e.g. all cells from a particular cell line) are the group means (e.g. cell line means).

Plot 914 illustrates the values of the disorder strength $L_d$ and the standard deviation of the disorder strength $\sigma L_d$ averaged over a cell for EGFR HT29 cells, control HT29 cells, and CSK HT29 cells in the $L_d$-$\sigma L_d$ parameter space. Each point in plot 914 corresponds to the disorder strength $L_d$ and the standard deviation of the disorder strength $\sigma L_d$ of a cell (e.g., averaged over ~400 channels). As can be seen in plot 914, different genetic variations of H29 cell type covers a separate regime in the $L_d$-$\sigma L_d$ parameter space with the more aggressive CSK-knockdown cells having the higher disordered nanoarchitecture as quantified by high $L_d$ and $\sigma_c$. Overall, an increase in one or more of $L_d$ and $\sigma_c$ indicates an increased malignant potential of the cell lines.

Thus, the three genetic variations of HT29 cells can be identified via determining the disorder strength $L_d$ and the standard deviation of the disorder strength $\sigma L_d$ of the corresponding cell. The inset of plot 914 is an amplification of the main plot 914 for the region of small disorder strength $L_d$ and the standard deviation of the disorder strength $\sigma L_d$ to show the separation between the two different types of HT29 cells.

Figure 9D:
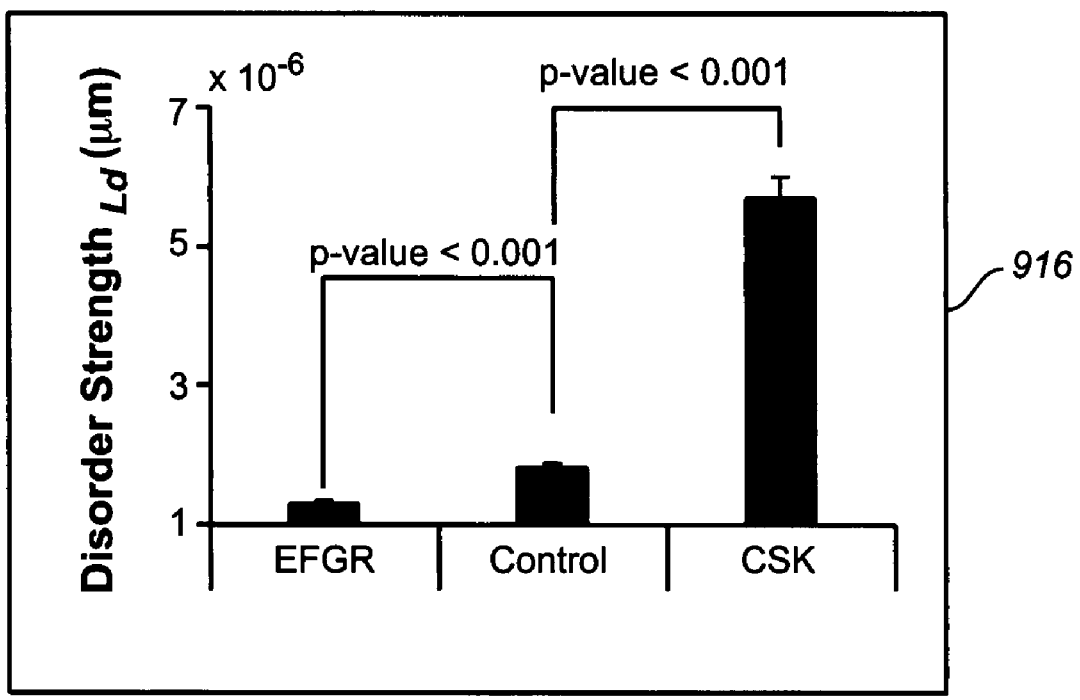
FIG. 9D are bar diagrams showing the disorder strength Ld and the standard deviation of the disorder strength $\sigma L_d$ for EGFR HT29 cells, control HT29 cells, and CSK HT29 cells, according to one embodiment.
Figure 9D:
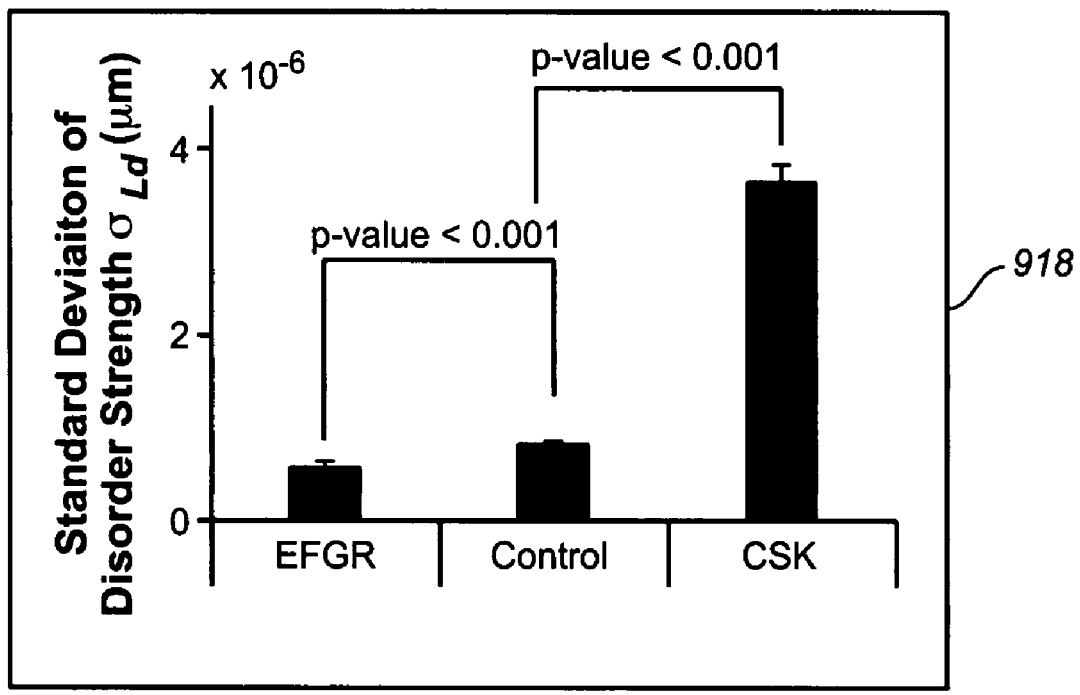

FIG. 9D are bar diagrams showing the disorder strength $L_d$ and the standard deviation of the disorder strength $\sigma L_d$ for EGFR HT29 cells, control HT29 cells, and CSK HT29 cells, according to one embodiment.

Plot 916 is a bar diagram of the average disorder strength $L_d$ for three types of HT29 cells obtained by averaging over ~30 cells that were randomly chosen for the three genetic variation of cell types. From the plot, a decrease in disorder strength $L_d$ for EGFR knockdown HT29 cells and increase for CSK knockdown cells can be observed. Plot 918 is a bar diagram of the standard deviation of the disorder strength $\sigma L_d$) averaged over ~30 cells for each cell types. The error bar represents the standard error of the mean. The standard deviation of disorder strength bar graphs show significant changes in standard deviation of disorder strength $\sigma L_d$ for normal and knock downed HT29 cells. For example, a decrease for EGFR knockdown HT29 cells and significant increase for CSK knockdown HT29 cells, relative to the $\sigma L_d$ value of control HT29 cells can be observed. Thus, in one embodiment, partial wave spectroscopy enables sensing architectural changes in otherwise histologically and/or cytologically indistinguishable but genetically different cells.

Carcinogen-Treated Animal Model

Animal models can be valuable in understanding pathophysiologic mechanisms and can be used for the development of diagnostic biomarkers and treatment strategies. In particular, animal models can be employed for studying the early stages of carcinogenesis. Therefore, animal studies are conducted with carcinogen-treated rats to determine the potential of partial wave spectroscopy for the diagnosis of early precancerous changes. For example, the azoxymethane (AOM) treated rat model has been used for studying colon carcinogenesis and developing diagnostic biomarkers and chemopreventive agents. The AOM-treated rat model is a suitable animal model of colon carcinogenesis because of the similarities in the morphological, genetic, and epigenetic alterations with human colon carcinogenesis.

In azoxymethane (AOM)-treated rats, colon carcinogenesis progresses through similar steps as in humans. For example, the earliest detectable marker of colon carcinogenesis, aberrant crypt foci, are precursor lesions which are observed on the colonic mucosal surface in both the AOM-treated rat model and in humans. In AOM-treated rats, aberrant crypt foci develop in ~8-12 weeks after the AOM injection, adenoma or carcinomas can be observed in 20-30 weeks, and carcinomas develop after 40 weeks. In human colon carcinogenesis, end-stage lesions (e.g., tumors, 40 weeks after AOM injection) may be symptomatic. Earlier lesions (e.g., adenoma or carcinomas, >20 weeks post AOM treatment) may not lead to symptoms but can be detected histologically via microscopic examination of biopsy. Thus, the science of molecular biology may push the frontiers of cancer detection even earlier since aberrant crypt foci can be detected as early as approximately 8 weeks after AOM treatment. However, no histological, molecular or genetic markers have so far been discovered to allow diagnosis earlier than 4-12 weeks after the initiation of carcinogenesis.

In this experiment, eighteen male Fisher 344 rats (150-200 g) were randomized equally to groups that received either 2 weekly intraperitoneal injections of AOM (15 mg/kg) or saline. Rats were fed standard chow and were killed at various times after the second injection (2, 5 and 8 weeks). Colons were removed from the rats and flushed with phosphate-buffered saline. Colonic epithelial cells were harvested utilizing a technique that combined chelation of divalent cations with mild mechanical dissociation. Briefly the colons were detached and washed with saline containing 1.0 mM dithiothreitol. The colons can then be ballooned up with the wash buffer and incubated in PBS at 37° C. for approximately 5 minutes. After draining the contents, the colonic sacs can be refilled with 100 mM PBS, pH 7.2 containing 1.5 mM EDTA and 0.5 mM dithiothreitol and incubated in PBS at 37° C. for approximately 15 minutes. Sacs were emptied and cells were collected by centrifugation at 500 g and then rinsed in appropriate buffer. Cells are routinely viable for approximately 1 hour after isolation. The measurements by partial wave spectroscopy can be taken on isolated colonic cells obtained at random from the colonic mucosa. To ascertain the viability of the cells, all the measurements were conducted within one hour after the cell extraction. All colonic epithelial cells were histologically normal.

Figure 10:
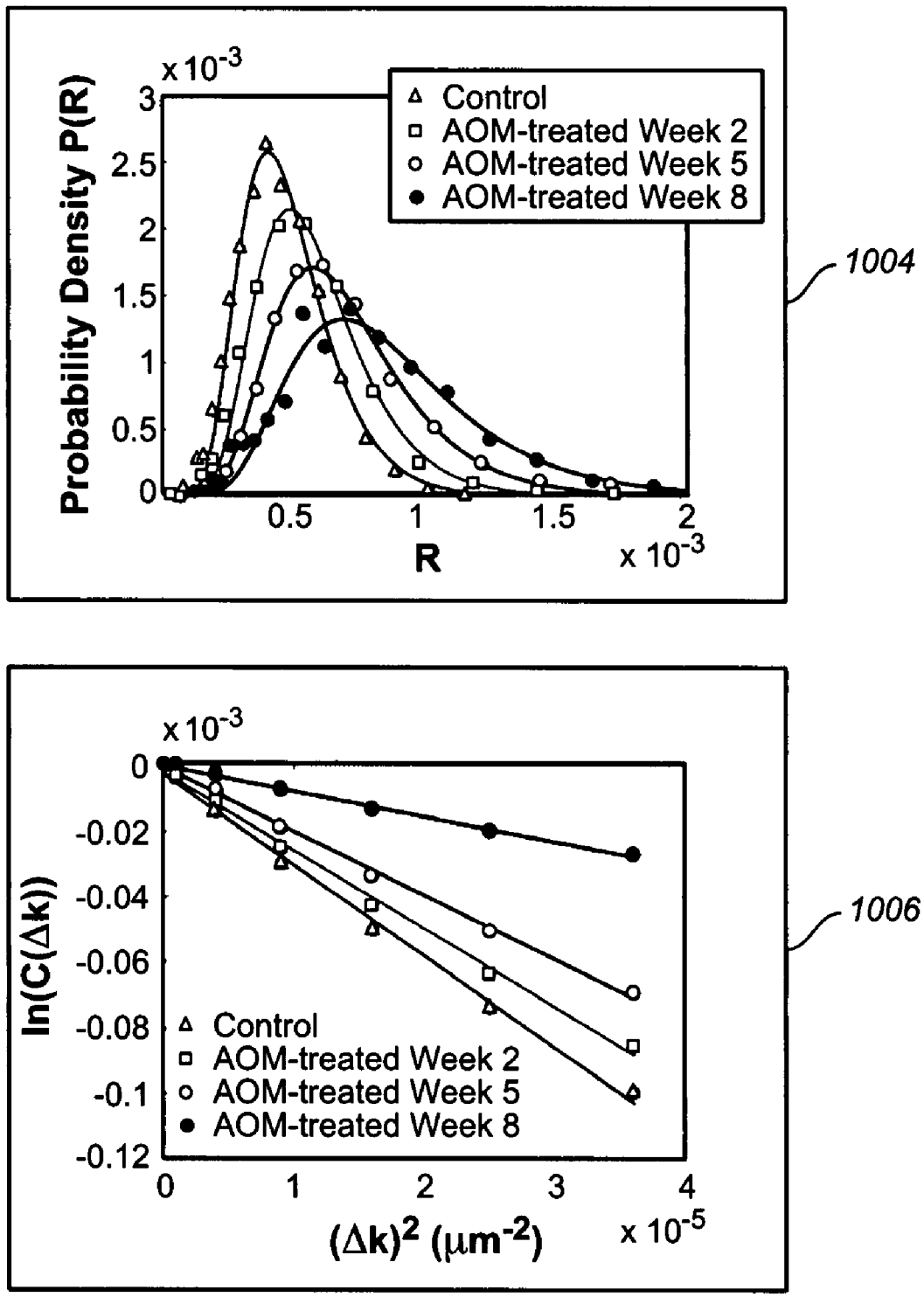
FIG. 10 illustrates a plot of the reflection coefficient spectra $R(\lambda)$ as a function of wavelength and plots of statistical parameters of the reflection coefficient spectra, determined from the intensity of the backscattered light recorded from colonic epithelial cells of control rats and AOM-treated rats, according to one embodiment.

FIG. 10 illustrates a plot of the reflection coefficient spectra $R(\lambda)$ as a function of wavelength and plots of statistical parameters of the reflection coefficient spectra, determined from the intensity of the backscattered light recorded from colonic epithelial cells of control rats and AOM-treated rats, according to one embodiment.

Plot 1004 shows the probability density function (p.d.f.) $P(R)$ of the reflection coefficient $R(\lambda)$ in the colonic epithelial cells of control and AOM-treated rats (2, 5, and 8 weeks after AOM treatment). The probability density function of $R(\lambda)$ from a cell can be calculated from the histogram analysis of $R(\lambda)$ from different parts of a cell. In this example, $R(\lambda)$ is calculated by averaging $R(\lambda)$ over wavelength ($\lambda$) from approximately 545 to 555 nm. for an image of approximately ~500 pixels/cell. Other bandwidths may be used for averaging. The reflection coefficients are determined to be on the order of 10-4-10-3, thus indicating that these biological cells could be considered as weakly disordered media.

The solid lines in plot 1004 are fitted curves for the probability density function $P(R)$ which is approximately log-normally distributed ($r^2 > 0.97$), as predicted by the 1D mesoscopic light transport theory. The log-normal distribution of the probability density function R may arise from phase changes and interference effects in the 1D reflection signals caused by the refractive index variation inside a biological cell. Plot 1006 shows the autocorrelation function $C(\Delta k)$ in colonic epithelial cells from control and AOM-treated rats at weeks 2, 5, and 8 respectively. On a log scale $C(\Delta k)$ approximately follows a linear dependence on $((\Delta k)^2$ with $r^2 > 0.99)$.

Figure 11:
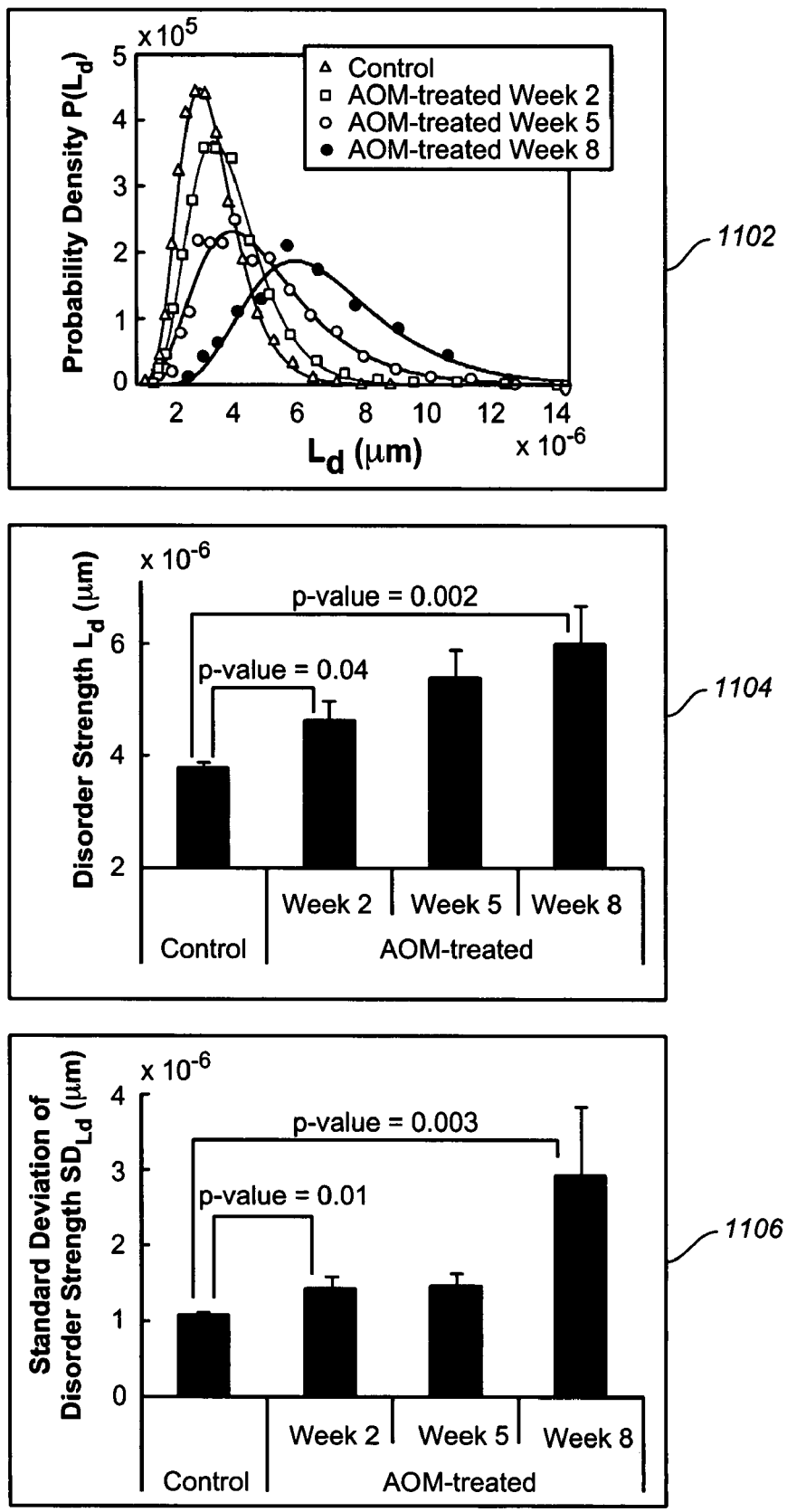
FIG. 11 are bar diagrams showing the disorder strength Ld and the standard deviation of the disorder strength $\sigma L_d$ of colonic epithelial cells obtained from control rats and AOM-treated rats, according to one embodiment.

FIG. 11 are bar diagrams showing the disorder strength $L_d$ and the standard deviation of the disorder strength $\sigma L_d$ of colonic epithelial cells obtained from control rats and AOM-treated rats, according to one embodiment.

Graph 1102 is a plot of the probability density function $P(L_d)$ of the disorder strength Ld in colonic epithelial cells for the control and AOM-treated rats at 2, 5, 8 weeks after AOM treatment, respectively, according to one embodiment. Thus in one embodiment, the distribution of $L_d$ can be determined to monitor the progression of carcinogenesis and to identify cell at different stages of carcinogenesis progression.

Graph 1104 is a bar diagram showing the change in the disorder strength Ld obtained from partial wave spectroscopy for the control and AOM-treated rats at 2, 5, 8 weeks after AOM-treatment, according to one embodiment. In this example, $L_d$ is averaged over approximately 20-30 cells at each time point. The error bars represent the standard error of the mean. As shown, at week two after AOM treatment, increase in disorder strength can be observed. The disorder strength continues to increase over time with increased exposure to AOM.

Graph 1106 is a bar diagram showing differences between the standard deviation $SDL_d$ in colonic epithelial cells for the control and AOM-treated rats at 2, 5, 8 weeks after AOM treatment, respectively. In this example, $L_d$ is averaged over approximately 20-30 cells at each time point. The error bars represent the standard error of the mean. At approximately week two after AOM treatment, increase in the standard deviation of the disorder strength is observable. The disorder strength continues to increase over time with increased exposure to AOM, indicating that the cells exposed to AOM is becoming progressively more heterogeneous with increase in time exposure to AOM, thus carcinogenesis. Such progressive and statistically significant alterations of the disorder strength indicate that the changes in $L_d$ and $SDL_d$ are unlikely due to an acute action of AOM. Thus, in one embodiment, the statistical parameters (e.g., $L_d$ and $SDL_d$) determined from light backscattered from the cells in question can be used as potential markers to detect early precancerous transformations in colonic epithelial cells. Note that the time point for a detectable alteration of the disorder strength and the standard deviation of disorder strength (e.g., 2 weeks after AOM-treatment) precedes the development of currently known histological and molecular markers.

Figure 12:
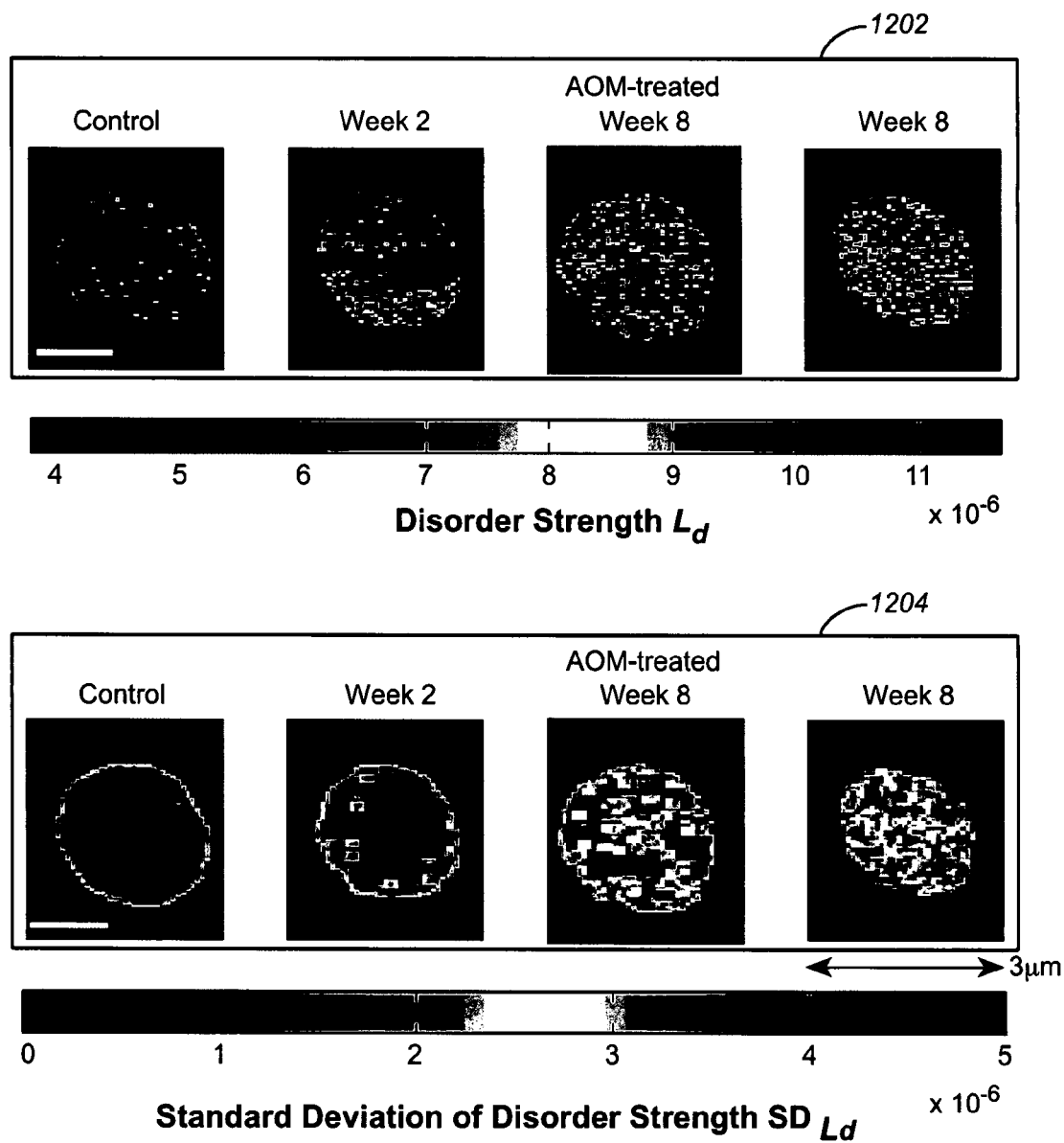
FIG. 12 illustrates images showing the spatial distribution of the disorder strength Ld and the standard deviation of the disorder strength $\sigma L_d$ in histologically normal, colonic epithelial cells recorded from control and AOM-treated rats (2, 5, and 8 weeks after carcinogenesis initiation), according to one embodiment.

FIG. 12 illustrates images showing the spatial distribution of the disorder strength $L_d$ and the standard deviation of the disorder strength $\sigma L_d$ in histologically normal, colonic epithelial cells recorded from control and AOM-treated rats (2, 5, and 8 weeks after carcinogenesis initiation), according to one embodiment.

The set of images 1202 show the spatial distribution of the disorder strength $L_d$ at each pixel with respect to the neighboring pixels in colonic epithelial cells from control and AOM-treated rats at 2, 5, and 8 weeks after AOM injection. The set of images 1204 show the spatial distribution of the standard deviation of the disorder strength $SDL_d$ at a number of pixels comprising colonic epithelial cells obtained from control and AOM-treated rats at 2, 5, and 8 weeks after AOM injection. As can be seen, progressive differences in both disorder strength and the standard deviation of disorder strength of colonic cells can be observed within weeks of exposure to AOM. An increase in the disorder strength typically indicates that the cellular organization is becoming increasingly heterogeneous. The increase in disorder strength, in one embodiment, can be used to identify alterations in cellular organization due to carcinoma and/or adenoma earlier than can be currently detected by conventional histopathology.

Thus, in one embodiment, partial wave spectroscopy can provide details about the nanoscale architecture from single living cells, for example, without need for fixation. The shift in the disorder length $L_d$ distribution between control and precancerous cells indicates that the development of carcinogenesis can be identified, in one embodiment, with increasing disorder strength and progressively higher heterogeneity of the cellular nanoarchitecture. The changes can be detected during the early stage of colon carcinogenesis (e.g., 2 weeks) after AOM injection. The change in disorder length can be observed at a time scale that is earlier than typically possible using other cellular or histological markers, which in some cases, can be identified at about 4-6 weeks. The nanoscale alterations as reflected by the disorder length may likely represent the epigenetic/genetic changes of "field carcinogenesis" that are the hallmarks of both the human disease and the AOM-treated rat model.

In one embodiment, the increase in disorder strength can be identified from broadening in the distribution of the probability density function $P(R)$. In one embodiment, the increase in disorder strength is further identified via the shift of the mean of the distribution of the probability density function $P(R)$ to higher value and an extended log-normal tail, as illustrated in plot 1004, in agreement with the prediction of mesoscopic light transport theory.

A higher disorder strength can be caused by the increase in the refractive index fluctuation $<\Delta n^2>$ and/or refractive index correlation length $l_c$. Thus, in one embodiment, by determining the disorder strength, changes occurring in a cell early in the process of precancerous transformation can be identified. In particular, for example, a higher $<\Delta n^2>$ may be associated with the increased density of intracellular solids (e.g., DNA, RNA, proteins and lipids). Similarly, changes in $l_c$ may be due to macromolecule aggregation such as clumping of chromatin in the nucleus. For $\Delta n \sim 0.02$, which is typical for biological tissue, the correlation length in a colonic cell is in most instances, on the order of 10 nm, corresponding to the size of the fundamental building blocks of a cell such as protein complexes, cytoskeleton, and nucleosomes.

In one embodiment, characterization of the statistical properties of the heterogeneity of biological cells with partial wave spectroscopy, at the nanoscale, for example, can facilitate identifying the mechanisms of cancer. Furthermore, in one embodiment, partial wave spectroscopy can be performed on cytological samples for facilitating biological research and cancer detection.

FIG. 13 illustrates plots showing the variation of the disorder strength $L_d$ with the correlation length $l_c$ and refractive index fluctuations $<\Delta n^2>$, as determined by the 1D slab model, according to one embodiment.

Plot 1302 illustrates the sensitivity of the disorder strength to the correlation length $l_c$, according to one embodiment. The slab has a refractive index distributed randomly in approximately 200 layers with a constant background refractive index no $\sim 1.38$ and refractive index fluctuation as $<\Delta n>_{max}=0.02$. The correlation length of the refractive index $l_c$ is: $<\Delta n(L)\Delta n(L')> \cong <\Delta n^2>\exp[-|L-L'|/l_c]$, In this example, the correlation length is varied from 0 to 65 nm., such that $kl_c \ll 1$, where k is the wave number.

Plot 1304 illustrates the sensitivity of the disorder strength $L_d$ to the refractive index fluctuations $<\Delta n^2>$, according to one embodiment. In this example, an inhomogeneous dielectric slab with an approximate thickness of 5 μm. is used as the 1D slab model. In this example, the slab has refractive index distributed randomly in approximately 200 layers with a constant background refractive index $n_0 \sim 1.38$ and refractive index fluctuation as $\langle \Delta n \rangle_{max}$ 0.05. The effect of the homogeneous slab is removed. As illustrated, $L_d$ is linearly dependent on both $l_c$ and $\langle \Delta n^2 \rangle$. Thus, as can be seen, the disorder strength $L_d$ can be proportional to the correlation length at scales less than the diffraction limit, at the nanoscale, for example.

Figure 14A:
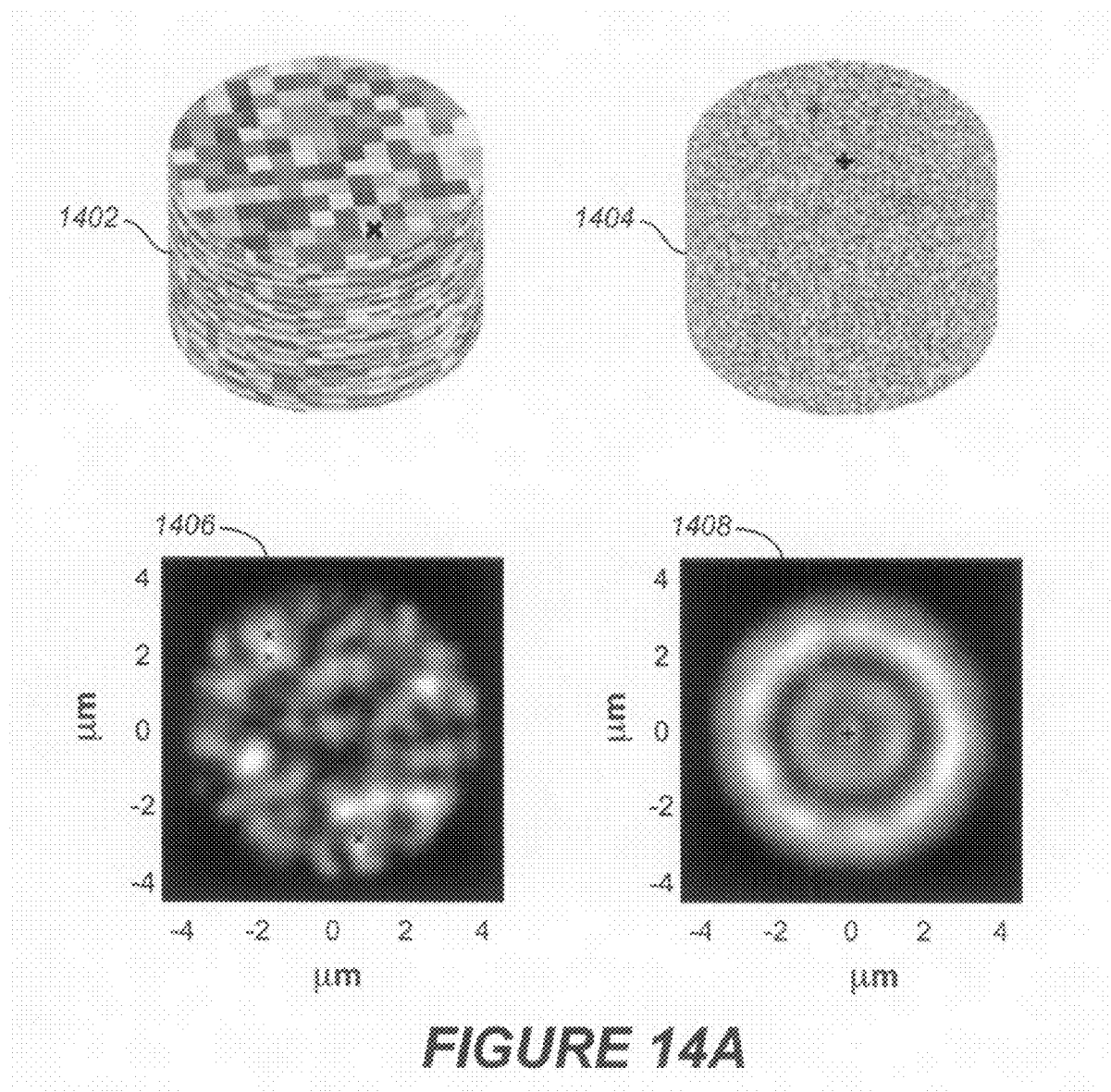
FIG. 14A illustrates examples of the geometry of elements used for FDTD simulations and synthesized backscattering images, according to one embodiment.

FIG. 14A illustrates examples of the geometry of elements used for FDTD simulations and synthesized backscattering images, according to one embodiment.

Elements 1402 and 1404 are inhomogeneous dielectric cylinders with diameter of 8 µm. and a height of 5 µm. In this example, the element 1402 is imported in the FDTD grid with a resolution of approximately 20 nm. Element 1402 has a random refractive index distribution in 600 nm.×600 nm.× 100 nm. rectangular blocks. Element 1404 has a random refractive index distribution in 60 nm.×60 nm.×60 nm. blocks. For both elements, the mean refractive index $n_0 \sim 1.38$ and the maximum refractive index fluctuation $\Delta n_{max} \sim 0.02$.

The synthesized backscattering images 1406 and 1408 are acquired by applying the vector diffraction theory to the far-field scattering fields calculated by FDTD.

FIG. 14B illustrates plots to compare the spectra obtained from FDTD simulations and the 1D slab model for analyzing the backscattered spectrum of a pixel of the image obtained from partial wave spectroscopy, according to one embodiment.

In the FDTD simulation performed in this example, the grid is terminated using a Berenger perfectly matched layer (PML) absorbing boundary condition. The total-filed/scattered-field technique can be employed to source an x-polarized plane wave propagating in the FDTD grid. A modified version of 3D near-to-far field transformation in the phasor domain can be implemented to determine the far-field scattered wave in the backward direction.

The set of plots 1410 illustrate comparisons of the FDTD-calculated backscattering spectra at 4 locations in the synthesized microscope image with that calculated by 1D slab model with vertical refractive index distribution following the corresponding location in the FDTD element. The set of plots 1412 illustrate comparisons of the point-spread function averaged FDTD-calculated backscattering spectra with the corresponding 1D slab model calculated spectra. The point spread function averaged FDTD spectra can be calculated as follows:

$$I_{FDTD}^{PSF}(\lambda) = \frac{\int_0^D \int_0^D PSF(x, y) I_{FDTD}(x, y, \lambda) dx dy}{\int_0^D \int_0^D PSF(x, y) dx dy},$$

where $I_{FDTD}(x, y, \lambda)$ is the spectrum determined via FDTD simulations at a pixel located at $(x, y)$ $PSF(x, y)$ is the point-spread function and $(x_0, y_0)$ was located at 4 different locations in the synthesized microscope image.

In one embodiment, the refractive index distribution in the 1D slab model can be calculated as:

$$n_{1D}^{PSF}(z) = \frac{\int_0^D \int_0^D PSF(x, y) n(x, y, z) dx dy}{\int_0^D \int_0^D PSF(x, y) dx dy},$$

where $n(x, y, z)$ is the refractive index at a pixel located at coordinates $(x, y, z)$ and $(x_0, y_0)$ was located at 4 locations in the synthesized microscope image.

Human Data

Human study was conducted by performing partial wave spectroscopy on cytological samples for pancreatic cancer diagnosis. Two signatures that can be measured in cells by means of partial wave spectroscopy and are diagnostic for pancreatic carcinogenesis: disorder strength of cell nano-architecture and the standard deviation of the disorder strength, were identified. These signatures can also be used for diagnosis of pancreatic cancer. Note that partial wave spectroscopy can be performed on either living, stained, and/or fixed cells.

The suboptimal sensitivity rates for the cytological diagnosis of pancreatic cancer is due in part to the relative rarity of frankly malignant-appearing cells that can be identified by cytology. However, cells that appear histologically normal may still have alterations in microscopically-invisible detail, at the nanoscale. To determine if epithelial cells considered to be nonmalignant by conventional cytology in patients with pancreatic cancer possess nanoscale abnormalities, archival pancreatic cytology slides previously obtained by fine needle aspiration (FNA) biopsy were used for screening via partial wave spectroscopy. The clinical history (including pancreatic cytology) of these patients was available. Thus, access to false negative cytology from patients who actually have pancreatic cancer is available.

In this experiment, the partial wave spectroscopy analysis of archival cytology specimens (e.g., fixed with alcohol) were obtained from 9 patients (3 control patients and 6 patients with pancreatic adenocarcinoma). The specimens obtained from the patients with pancreatic cancer include both cytologically malignant cancer cells and cytologically normal cancer cells.

After performing partial wave spectroscopy, the spatial distributions of the disorder strength $L_d$ within each cell was determined (e.g., $L_d(x,y,)$). Then average disorder strength $L_d$ for each given cell was calculated by averaging $L_d(x,y,)$ over all pixels $(x,y)$ for an image of a given cell. For each cell, the standard deviation of the disorder strength $\sigma_{Ld}$. within this cell can also be determined. Thus, each cell was characterized by the pair of parameters: disorder the disorder strength $L_d$ and the standard deviation of the disorder strength $\sigma L_d$.

Figure 15:
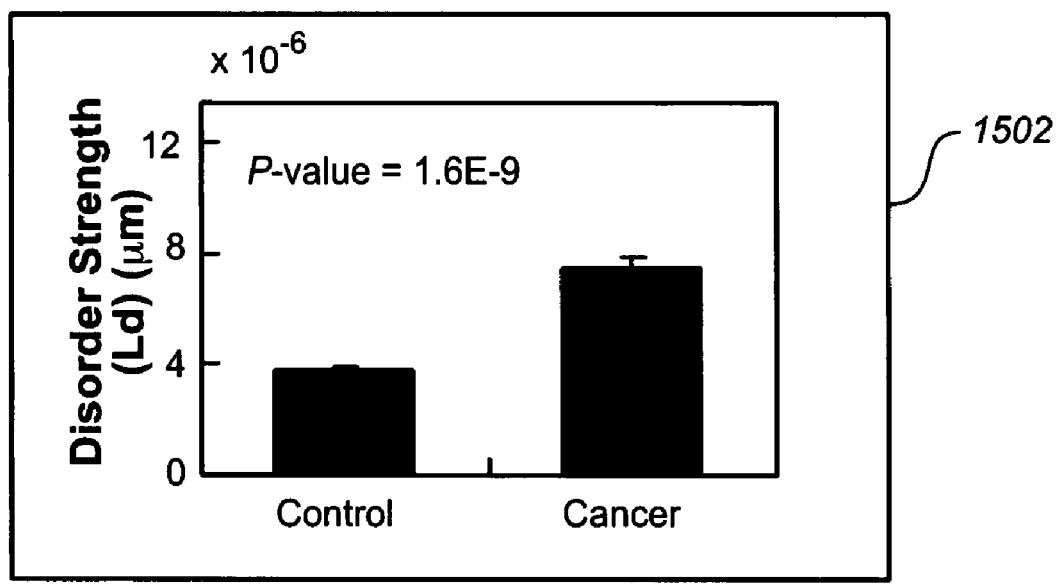
FIG. 15 are bar diagrams showing data obtained via partial wave spectroscopy of human samples where the disorder strength and the standard deviation of the disorder strength were plotted for cytologically malignant pancreatic cancer cells, according to one embodiment.
Figure 15:
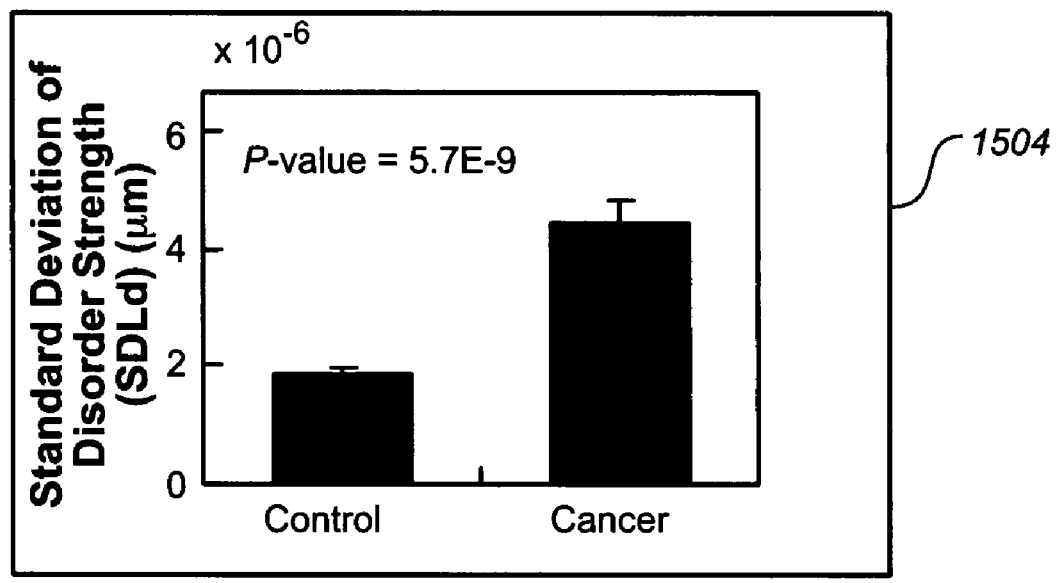

FIG. 15 contains bar diagrams showing data obtained via partial wave spectroscopy of human samples where the disorder strength and the standard deviation of the disorder strength were plotted for cytologically malignant pancreatic cells obtained from patients with pancreatic cancer vs. cytologically normal pancreatic cells obtained from patients without pancreatic cancer, according to one embodiment.

Graph 1502 is a bar diagram of the disorder strength $L_d$ of cytology specimens obtained from seven control patients vs. the disorder strength of cytology specimens obtained from nine patients with pancreatic adenocarcinoma. Graph 1504 is the bar diagram of the standard deviation of the disorder strength $\sigma_{Ld}$ of cytology specimens obtained from seven control patients vs. standard deviation of the disorder strength of cytology specimens obtained from nine patients with pancreatic adenocarcinoma.

Figure 16:
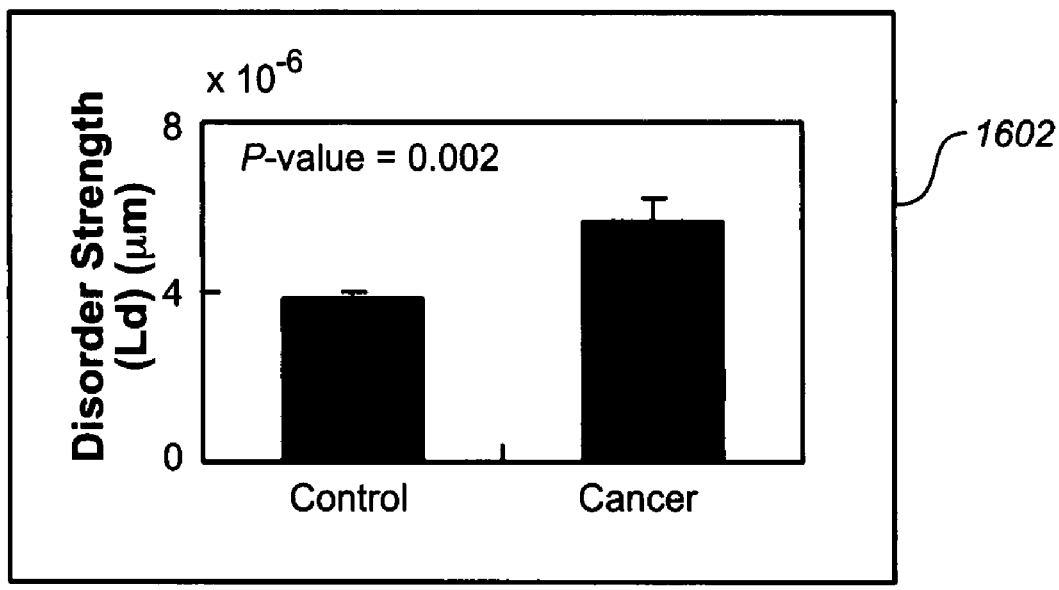
FIG. 16 are bar diagrams showing data obtained via partial wave spectroscopy of human samples where the disorder strength $L_d$ and the standard deviation of the disorder strength $\sigma L_d$ were plotted for cytologically normal pancreatic cancer cells, according to one embodiment.
Figure 16:
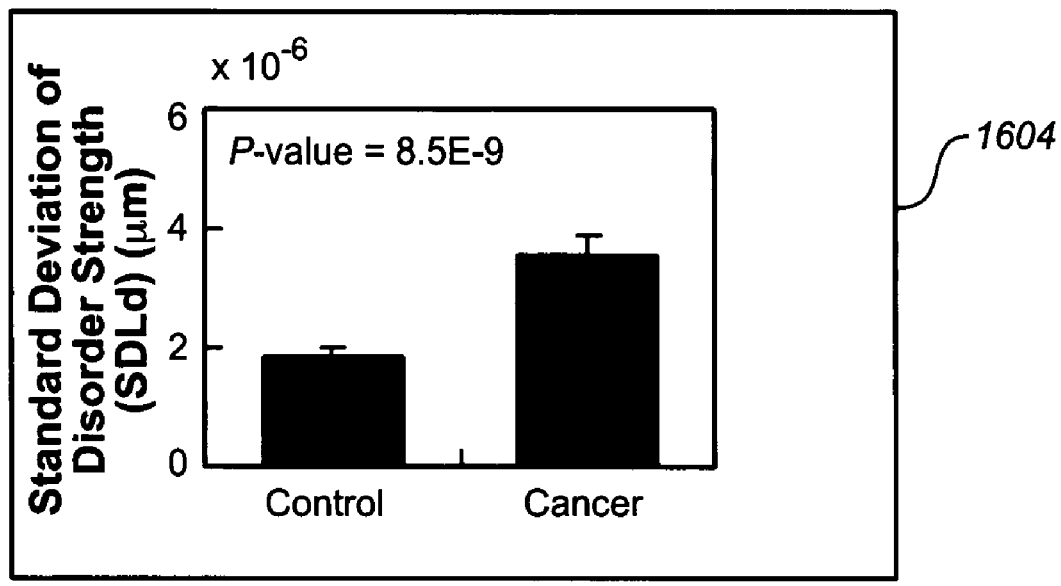

FIG. 16 are bar diagrams showing data obtained via partial wave spectroscopy of human samples where the disorder strength $L_d$ and the standard deviation of the disorder strength $\sigma_{Ld}$ were plotted for cytologically normal pancreatic cells obtained from patients with pancreatic cancer vs. cytologically normal pancreatic cells obtained from patients without pancreatic cancer, according to one embodiment.

Graph 1602 is the bar diagram of the disorder strength $L_d$ of cytology specimens obtained from nine control patients vs. the disorder strength of cytology specimens obtained from ten patients with pancreatic adenocarcinoma. Graph 1604 is the bar diagram of the standard deviation of the disorder strength $\sigma_{L_d}$ of cytology specimens obtained from nine control patients vs. standard deviation of the disorder strength of cytology specimens obtained from ten patients with pancreatic adenocarcinoma. As can be seen from the figures, both disorder the disorder strength $L_d$ and the standard deviation of the disorder strength $\sigma L_d$ were significantly elevated in non-cytologically malignant cells obtained from patients with pancreatic cancer. Thus, the presence of pancreatic cancer can be identified via partial wave spectroscopic analysis of pancreatic cells that were detected as cytologically normal, according to one embodiment. Partial wave spectroscopy can potentially revolutionize the cytological diagnosis of pancreatic cells through correct classification of cytologically non-malignant-appearing pancreatic cells as malignant.

In other embodiments of the present disclosure, partial wave spectroscopy is applicable to cancer detection and disease diagnosis in a number of organs from which cells can be obtained. The examples of such organs from which cellular samples can be currently obtained for cytological diagnosis include, but are not limited to, the cervix, breast, prostate, oral cavity, esophagus, lung, bladder etc.

For example, one of the difficulties associated with the detection of bladder cancer is that although cells shaded from the bladder mucosa are easily collected from patient's urine. However, cytology cannot distinguish dysplastic (precancerous) and nondysplastic bladder cells. Therefore, one of the reliable means of detecting dysplasia in the bladder is through biopsy, requiring insertion of a catheter into the urethra, which is painful and invasive. Thus, a technique enabling differentiation between dysplastic and normal bladder cells in cytological samples will potentially have a major impact on the management of bladder cancer. Furthermore, spectroscopic cytology can potentially be used to assist in the analysis of cytologic samples routinely obtained to diagnose cancer in a variety of other organs including the lung, breast, and esophagus.

The difficulties associated with pancreatic cancer detection can potentially be addressed by the implementation of back-scattering spectroscopic microscopy for the analysis of cells obtained from the pancreas. For example, cells from a pancreatic duct can be obtained by means of aspiration of shed cells in pancreatic juice that can be collected by a brush introduced through the ampulla of Vater following i.v. injection of secretin, which induces the production of pancreatic juice. As currently performed, the sensitivity of pancreatic cytology is unacceptably low (i.e., <50%). An improved cytological diagnosis can be achieved by means of enhancing cytology with optical spectroscopy, e.g., light scattering spectroscopic microscopy. One of the advantages of spectroscopically assisted cytology is that it offers the possibility to assess cell architecture at length scales far below the resolution of conventional microscopic cytology—up to a few nanometers.

Field Effect

Some cancer risk stratification techniques exploit the "field effect," the concept that assessment of biomarkers in one area of the colon should be able to determine the likelihood of current/future neoplastic lesions throughout the colon. For example, the genetic/environmental milieu that results in a neoplastic lesion in one area of the colon can be detectable in uninvolved (e.g., colonoscopically, histologically, and/or endoscopically normal-appearing) mucosa throughout the colon.

There exists evidence to support the molecular underpinnings of the microarchitectural changes noted in the histologically and/or endoscopically normal "field." For instance, Chen et al. recently reported that a panel of proto-oncogenes, including cyclooxygenase 2 and osteopontin, were markedly over expressed in histologically and/or endoscopically normal mucosa of patients harboring colorectal cancer. This is also noted in the preneoplastic MIN mouse and, importantly, the magnitude of proto-oncogenes over-expression was in-between control intestinal epithelium (C57BL/6 mice wild type at APC) and adenomatous tissue or carcinomous tissue, arguing for the relevance of these changes to tumorigenesis. Furthermore, epigenetic events (e.g., loss of insulin growth factor II imprinting) can be increased in the uninvolved mucosa of patients with who harbored adenoma or carcinomas.

A commonly used clinical example is the identification of the distal adenoma or carcinoma on flexible sigmoidoscopy to predict the occurrence of neoplasia in the proximal colon. Other attempts include correlation of rectal aberrant crypt foci (ACF) using chromoendoscopy with colonic adenomas and carcinomas. Unfortunately, the performance characteristics of the existing markers remain suboptimal (e.g., the sensitivity and positive predictive value for the ability of flexible sigmoidoscopy to detect advanced proximal lesions are 40% and 6%, respectively).

Thus, currently available morphologic markers for the field effect are inadequate for risk stratification. Several lines of evidence suggest that the field effect has the potential of being sensitive at identifying patients with colonic neoplasia. Studies have reported that in the histologically and/or endoscopically normal mucosa of subjects harboring colonic neoplasia, there are profound genetic and epigenetic alterations in the field effect. However, detecting these molecular events with a methodology that would be feasible in clinical practice has been challenging.

Interrogation of the pancreatic duct for pancreatic cancer screening introduces risk of acute pancreatitis. The adjacent periampullary duodenal mucosa can be accessed via existing upper endoscopy means and the examination of which presents a possibility to diagnose presence of pancreatic neoplasia without the potential risk of pancreatitis or other serious complications. Based on the field-effect, a neoplastic lesion in a particular tissue site such as the pancreas, can be detectable in the duodenal mucosa adjacent to the ampulla. The duodenal mucosa can be examined in vivo or ex vivo (e.g., from tissue biopsy samples obtained from endoscopy means).

In one embodiment, partial wave spectroscopy can be used to identify colon carcinogenesis risk throughout the colon through detection of the field effect. Data obtained from azoxymethane-treated rat model of colon carcinogenesis show alterations in partial wave spectroscopy data at time points that precede ACF or adenoma or carcinoma formation. Furthermore, these markers progress over time consonant with the progression of carcinogenesis.

In human studies, partial wave spectroscopic analysis of the cytologically normal mucosa is observed to be able to detect differences in patients who harbored adenoma or carcinomas when compared with those who were neoplasia free. Thus, the technical advance of partial wave spectroscopy may potentially translate into a practical means for colon cancer screening. As discussed, the exploitation of the field effect is a strategy in colorectal cancer screening (e.g., assessment of distal adenoma or carcinomas or ACF).

In one embodiment, the analysis of mucosal nanoarchitectural and microarchitectural markers by means of partial wave spectroscopy exceeded, in terms of detection relative to the stage of progression, the analysis of classic morphologic and/or biochemical markers. For example, the risk of neoplasia was assessed in the visually normal colonic mucosa rather earlier than the detection of morphologic lesions (polyps). The neoplastic transformation may lead to various types of cancer, such as pancreatic cancer, colon cancer, liver cancer, lung cancer, esophageal cancer, stomach cancer, cervical cancer, oral cavity cancer, ovarian cancer, breast cancer, bladder cancer, cholangiocarcinoma, prostate cancer, and/or head and neck cancer, which can be detected via partial wave spectroscopy screening.

Figure 17:
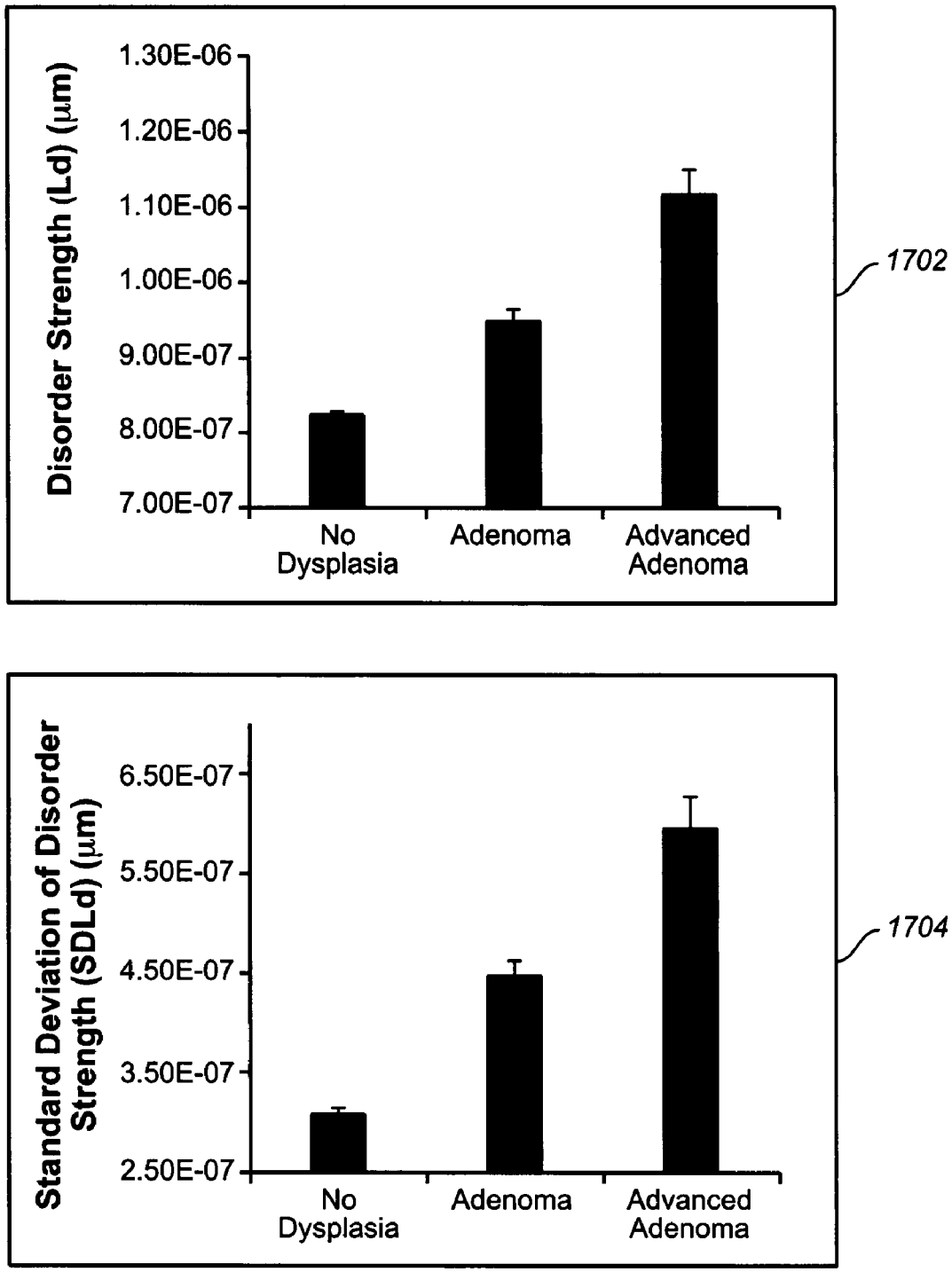
FIG. 17 are bar diagrams of the disorder strength Ld and the standard deviation of the disorder strength $\sigma L_d$ of cells obtained from normal-appearing rectal mucosa of patients via partial wave spectroscopy with no adenoma or carcinoma, non-advanced adenoma or carcinoma, and advanced adenoma or carcinoma, anywhere in the colon, according to one embodiment.

FIG. 17 are bar diagrams of the disorder strength Ld and the standard deviation of the disorder strength σLd of cells obtained from normal-appearing rectal mucosa of patients via partial wave spectroscopy with no adenoma or carcinoma, non-advanced adenoma or carcinoma, and advanced adenoma or carcinoma, anywhere in the colon, according to one embodiment.

Identification of colon carcinogenesis can be performed via partial wave spectroscopy on ex vivo tissue obtained from human subjects undergoing colonoscopy. In this experiment, the cells to be imaged by partial wave spectroscopy were brushed from normal-appearing rectal mucosa. In addition, partial wave spectroscopy data can also be obtained from tissue of the ascending colon, hepatic flexure, transverse colon, splenic flexure, descending colon, and/or sigmoid colon to detect adenoma or carcinoma in the colon. Eleven patients were noted to have non-advanced adenoma or carcinomas on current colonoscopy, four patients have advanced adenoma or carcinoma, and twenty patients did not have carcinoma, as determined by colonoscopy.

As can be seen in plots 1702 and 1704, the disorder strength $L_d$ and the standard deviation of the disorder strength $\sigma L_d$ in cancer patients were increased in patients with adenoma or carcinomas, and further increased for patients with advanced adenoma or carcinoma. By performing partial wave spectroscopy, an increase in the disorder strength and the standard deviation of the disorder strength obtained from normal-appearing rectal mucosa in patients who harbored adenoma or carcinomas in their colon can be observed when compared with those who were neoplasia free, or with less advanced adenoma/carcinoma.

Figure 18:
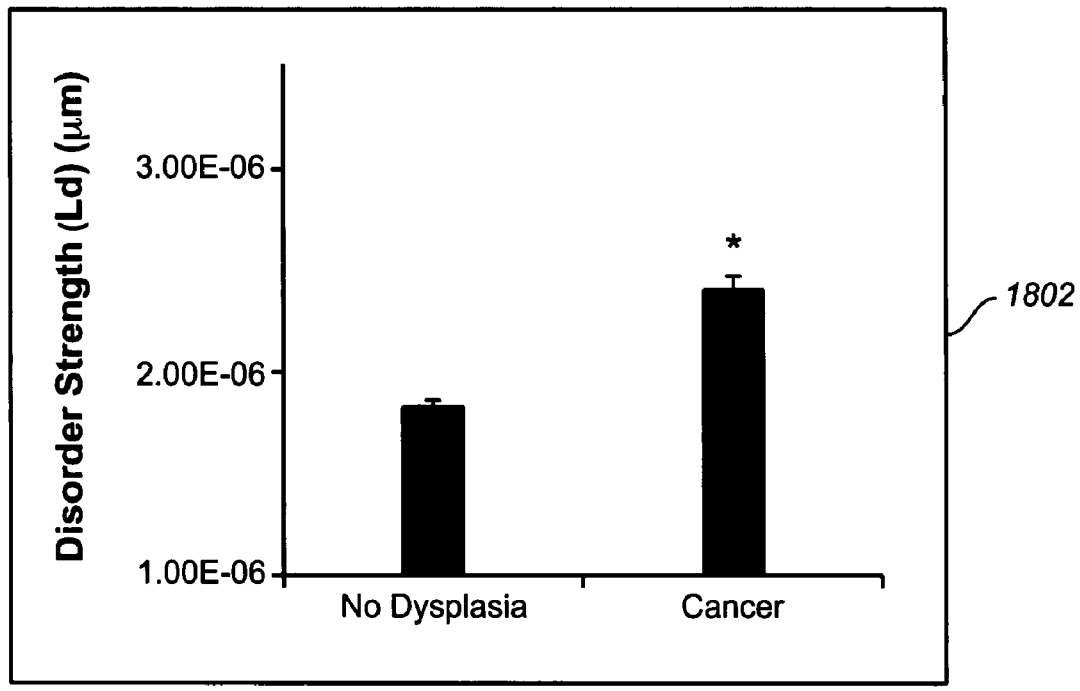
FIG. 18 are bar diagrams of the disorder strength Ld and the standard deviation of the disorder strength $\sigma L_d$ of cells obtained from normal-appearing duodenal periampullary mucosa from patients with pancreatic cancer and control patients with no dysplasia, according to one embodiment.
Figure 18:
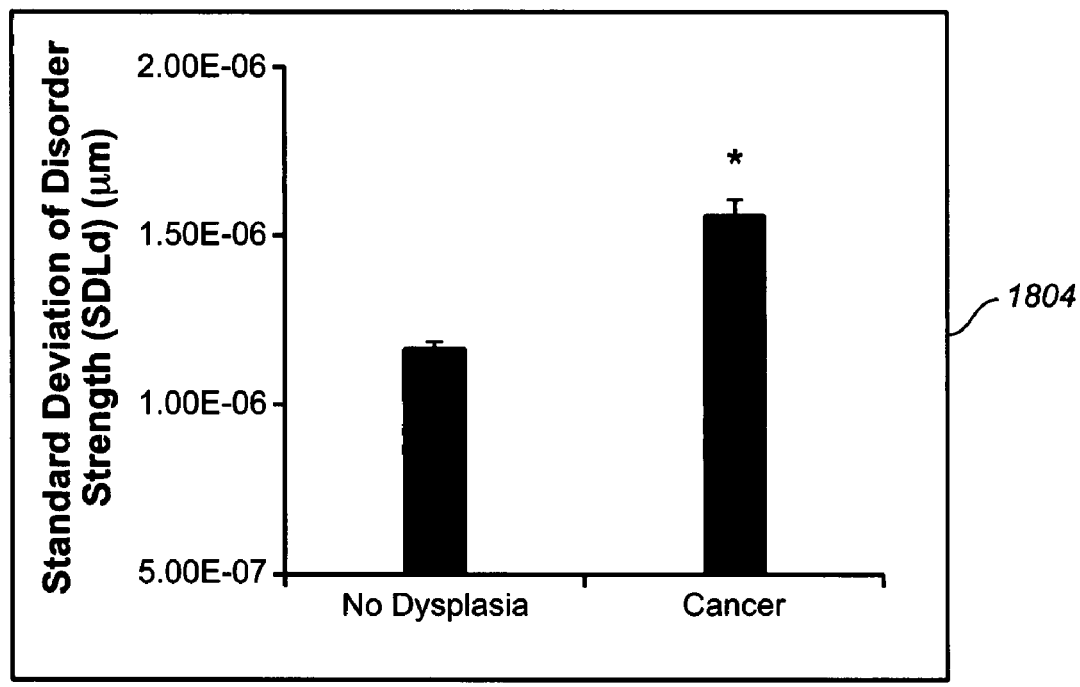

FIG. 18 are bar diagrams of the disorder strength $L_d$ and the standard deviation of the disorder strength $\sigma L_d$ of cells obtained from normal-appearing duodenal periampullary mucosa from patients with pancreatic cancer and control patients with no dysplasia, according to one embodiment.

In one embodiment, partial wave spectroscopy can be performed on cells obtained from biopsies taken from the normal-appearing duodenal periampullary mucosa in patients undergoing an upper endoscopic procedure who have pancreatic cancer (positive group) and those with no history of pancreatic disease or cancer (negative controls). This experiment was performed on 26 patients with no pancreatic cancer and 10 patients with pancreatic cancer. The presence or absence of pancreatic cancer was determined by clinical history or during surgery. The cells were smeared on a glass surface and fixed, according to conventional cytology protocol and partial wave spectroscopy can be performed on these duodenal cytology slides. On average, ~50 cells per patient were obtained and assessed in this experiment.

As shown in plots 1802 and 1804, the disorder strength $L_d$ and the standard deviation of the disorder strength $\sigma L_d$ assessed from the periampullary mucosa is higher for patients with pancreatic cancer as compared with control patients who were cancer-free. Therefore, identification of patients harboring PC can be achieved by minimally invasive and very low risk duodenal brushing that can be performed during upper endoscopy without the need to interrogate the pancreas, which would ideal for a screening of asymptomatic patients. Thus, in one embodiment, partial wave spectroscopy can be used to identify pancreatic cancer via imaging duodenal periampullary mucosa, through the field effect. The imaged duodenal periampullary mucosa may appear normal, or abnormal.

Figure 19:
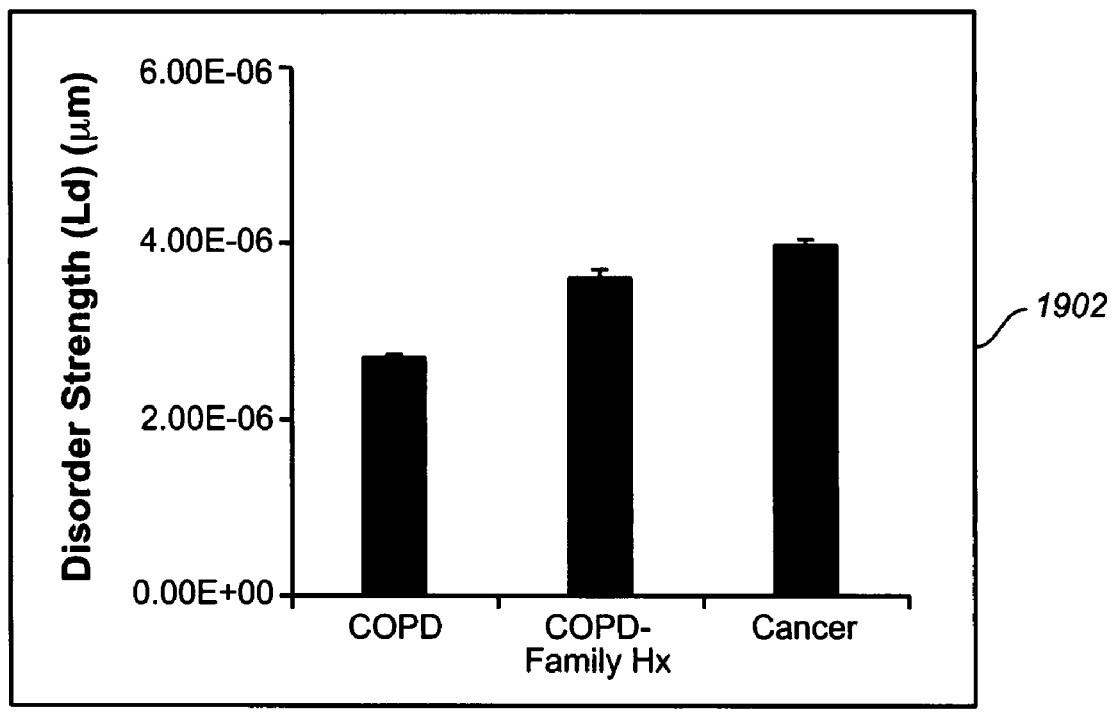
FIG. 19 are bar diagrams of the disorder strength Ld and the standard deviation of the disorder strength $\sigma L_d$ of cells obtained from normal-appearing buccal (cheek) mucosa from patients with lung cancer, COPD and no lung cancer, and patients with no lung cancer but a family history of lung cancer, according to one embodiment.
Figure 19:
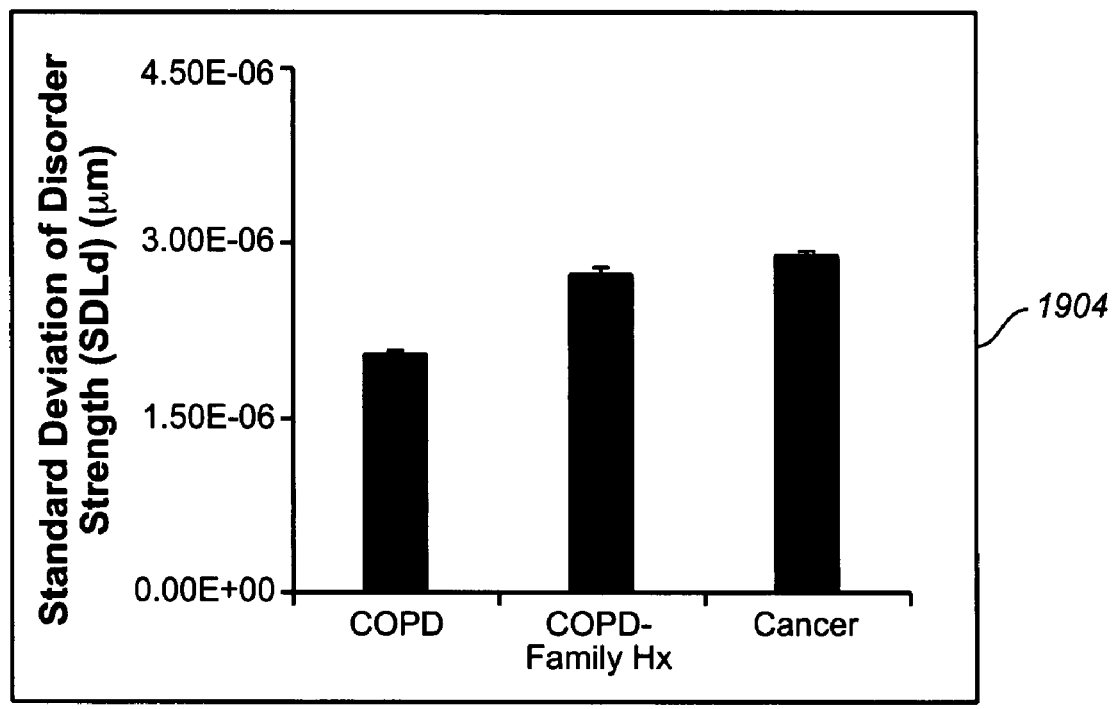

FIG. 19 are bar diagrams of the disorder strength $L_d$ and the standard deviation of the disorder strength $\sigma L_d$ of cells obtained from normal-appearing buccal (cheek) mucosa from patients with lung cancer, COPD and no lung cancer, and patients with no lung cancer but a family history of lung cancer, according to one embodiment.

In one embodiment, partial wave spectroscopy can be utilized for lung cancer screening via examining cells brushed from normal-appearing buccal mucosa. In this experiment, partial wave spectroscopy was performed on 16 patients with no lung cancer but with chronic obstructive pulmonary disease (COPD), 7 patients with no lung cancer and a family history of lung cancer, and 19 patients with lung cancer. As shown in plots 1902 and 1904, the disorder strength and the standard deviation of the disorder strength assessed from the buccal mucosa is higher for patients with lung cancer as compared with control patients who were cancer-free. In addition, the disorder strength and the standard deviation of the disorder strength assessed from the buccal mucosa is higher for patients without lung cancer but with a family history of lung cancer as compared with control patients who were cancer-free. Therefore, in one embodiment, identification of patients harboring lung cancer or a risk of lung cancer can be achieved by removing a sample of cells from the lining of the cheek for study.

Although embodiments have been described with reference to specific exemplary embodiments, it will be evident that the various modification and changes can be made to these embodiments. Accordingly, the specification and drawings are to be regarded in an illustrative sense rather than in a restrictive sense. The foregoing specification provides a description with reference to specific exemplary embodiments. It will be evident that various modifications may be made thereto without departing from the broader spirit and scope as set forth in the following claims. The specification and drawings are, accordingly, to be regarded in an illustrative sense rather than a restrictive sense.

LIST OF REFERENCES

Abrahams E., Anderson P. W., Licciardello D. C. & Ramakrishnan T. V. "Scaling theory of localization—absence of quantum diffusion in 2 dimensions." Phys. Rev. Lett. 42, 673-676 (1979).

Abrikosov A. A. & Ryzhkin I. A. "Conductivity of quasi-one-dimensional metal systems." Adv. Phys. 27, 147-230 (1978).

Aliperti G. "Complications related to diagnostic and therapeutic endoscopic retrograde cholangiopancreatography," Gastrointest Endosc Clin N Am 6(2), 379-407 (1996).

Anderson P. W. "Absence of diffusion in certain random lattices." Phys. Rev. 109, 1492-1505 (1958).

Anderson P. W., Thouless D. J., Abrahams E. & Fisher D. S. "New method for a scaling theory of localization." Phys. Rev. B 22, 35 19-3526 (1980).

Backman V. et al. "Detection of pre invasive cancer cells." Nature 406, 35-36 (2000).

Barber P. W. and Hill S. C., "Light Scattering by Particles: Computational Methods, Advanced Series in Applied Physics," World Scientific (1990).

Berenger J. P. "A perfectly matched layer for the absorption of electromagnetic waves." J. Comput. Phys. 114, 185-200 (1994).

Boustany N. N., Kuo S. C., and Thakor N. V., Opt. Lett. 26, 1063 (2001).

Brand R. E., and Matamoros A. "Imaging techniques in the evaluation of adenocarcinoma of the pancreas," Dig Dis Sci 16, 242-252 (1998).

"Cancer Facts & FIGS. 2005," American Cancer Society (2005).

Chen L., Hao C., Chiu Y., Wong P., Melnick J., Brotman M., Moretto J., Mendes F., Smith A., Bennington J., Moore D., and Lee N. "Alteration of Gene Expression in Normal-Appearing Colon Mucosa of APCmin Mice and Human Cancer Patients," Cancer Research 64, 3694-3700 (2004).

Coffey D. S. "Self-organization, complexity and chaos: The new biology for medicine." Nat. Med. 4, 882-885 (1998).

Curry A., Nusz G., Chilkoti A., and Wax A., Opt. Express 13, 2668 (2005).

DeWitt J., Devereaux B., Chriswell M., and e. al., "Comparison of endoscopic ultrasonography and multidetector computed tomography for detecting and staging pancreatic cancer," Ann Intern Med 141, 753-763 (2004).

Drezek R. et al. "Light scattering from cervical cells throughout neoplastic progression: influence of nuclear morphology, DNA content, and chromatin texture." Journal of Biomedical 8, 7-16 (2003).

Eloubeidi M. A., Chen V. K., Eltoum I. A. and e. al., "Endoscopic ultrasound-guided fine needle aspiration biopsy of patients with suspected pancreatic cancer: diagnostic accuracy and acute and 30-day complications," Am J Gastroenterol 98, 2663-2668 (2003).

Feng S. C., Kane C., Lee P. A. & Stone A. D. "Correlations and fluctuations of coherent wave transmission through disordered media." Phys. Rev. Lett. 61, 834-837 (1988).

Foerster E. C., Trommer P., Schneider M. U., Matek W., Gerner G., and Domschke W., "Transpapillary miniscopy and mini-biopsy of the pancreatic duct," Endoscopy 22, 78-80 (1990).

Gurjar R. S. et al. "Imaging human epithelial properties with polarized light scattering spectroscopy." Nat. Med. 7, 1245-1248 (2001).

Haley S. B. & Erdos P. Wave-propagation in one-dimensional disordered structures. Phys. Rev. B 45, 8572-8584 (1992).

Hingorani, S. R., Petricoin, E. F., Maitra, A., and e. al., "Pre invasive and invasive ductal pancreatic cancer and its early detection in the mouse," Cancer Cell 4, 437-450 (2003).

Jemal A., Tiwari R. C., Murray T., Ghafoor A., Samuels A., Ward E., Feuer E. J., and Thun M. J. "Cancer statistics, 2004," CA Cancer J Clin 54(1), 8-29 (2004).

Kim J. E., Lee K. T., Lee J. K., Paik S. W., Rhee J. C., and Choi K. W. "Clinical usefulness of carbohydrate antigen 19-9 as a screening test for pancreatic cancer in an asymptomatic population," J Gastroenterology Hepatology 19, 182-186 (2004).

Kim Y. L., Liu Y., Turzhitsky V. M., Wali R. K., Roy H. K. and Backman V. "Depth-resolved Low-coherent Backscattering in Tissue," Optics Letters 30(7), 741-743 (2005).

Kim Y. L., Pradhan P., Subramanian H., Liu Y., Kim M. H., and Backman V. "Experimental evidence of the minimal scattering events in enhanced backscattering of light in discrete random media," Phys Rev Lett, submitted (2005).

Kim Y., Liu Y., Wali R., Roy H., and Backman V. "Coherent Backscattering Spectroscopy," Optics Letters 29(16), 1906-1908 (2004).

Kim Y., Liu Y., Wali R., Roy H., and Backman V. "Low-Coherent Backscattering Spectroscopy for Tissue Characterization," Applied Optics 44(3), 366-377 (2005).

Kim Y., Liu Y., Wali R., Roy H., Goldberg M., Kromine A., Chen K., and Backman V. "Simultaneous Measurement of Angular, Spectral, and Azimuthal Dependence of Light Scattering for Characterization of Tissue Micro architecture and its Alteration in Early Pre cancer," IEEE J. Select. Top. Quant. Elect. 9(2), 243-257 (2003).

Kishimoto Y., Morisawa T., Hosoda A., Shiota G., Kawasaki H., and Hasegawa J. "Molecular changes in the early stage of colon carcinogenesis in rats treated with azoxymethane," J Exp Clin Cancer Res 21(2), 203-211 (2002).

Kobaek-Larsen M., Thorup I., Diederichsen A., Fenger C. & Hoitinga M. R. "Review of colorectal cancer and its metastases in rodent models: Comparative aspects with those in humans." Comparative Med. 50, 16-26 (2000).

Kramer B. & Mackinnon A. "Localization —theory and experiment." Rep. Prog. Phys. 56, 1469-1564 (1993).

Kumar N. "Resistance fluctuation in a one-dimensional conductor with static disorder." Phys. Rev. B 31, 5513-5515 (1985).

Leblanc J. K., Ciaccia D., Al-Assi M. T., and e. al., "Optimal number of EUS-guided fine needle passes needed to obtain a correct diagnosis," Gastrointest Endosc 59, 475-48 1 (2004).

Lee P. A. & Ramakrishnan T. V. "Disordered electronic systems." Rev. Mod. Phys. 57, 287-337 (1985).

Li X. D., Boppart S. A., Van Dam J., Mashimo H., Mutinga M., Drexler W., Klein M., Pitris C., Krinsky M. L., Brezinski M. E., and Fujimoto J. G., Endoscopy 32, 921 (2000).

Li X., Chen Z. G., Taflove A., and Backman V., Proc. SPIE 5693, 92 (2005).

Li X., Liu Y., Kim Y. L., Taflove A. & Backman V. in "Frontiers in optics 2005," The 89th OSA annual meeting JWA40 Tucson, AZ, USA, (2005).

Li X., Taflove A. & Backman V. "Modified FDTD near-to-far field transformation for improved backscattering calculation of strongly forward scattering objects." IEEE Antennas and Wireless Propagation Lett. 4, 35-38 (2005).

Li D., Xie K., Wolff R., and Abbruzzese J. L. "Pancreatic cancer," Lancet 363(9414), 1049-1057 (2004).

Liu Y., Li X., Kim Y. L. & Backman V. "Elastic backscattering spectroscopic microscopy." Opt. Lett. 30, 2445-2447 (2005).

Liu Y., Brand R. E., Kim Y. L., Turzhitsky V., Roy H. K., Hasabou N., Shah D., and Backman V. "Optical markers in duodenal mucosa predict the presence of pancreatic cancer," Clin Cancer Res, in press (2007).

Liu Y., Kim Y. L., and Backman V. "Development of a Bioengineered Connective Tissue Model and Its Application in the Investigation of the Depth Selectivity of Polarization-gating," Appl Optics 44(12), 2288-2299 (2005).

Liu, Y., Kim, Y. L., Li, X., and Backman V. "Investigation of Depth Selectivity of Polarization Gating for Tissue Characterization," Optics Express 13(2), 601-611 (2005).

Machida H., Sano Y., Hamamoto Y., Muto M., Kozu T., Tajiri H., and Yoshida S., "Narrow-band imaging in the diagnosis of colorectal mucosal lesions: a pilot study," Endoscopy 36(12), 1094-1098 (2004).

Maitra A., Ashfaq R., Gunn C. R., Rahman A., Yeo C. J., Sohn T. A., Cameron J. L., Hruban R. H., and Wilentz R. E. "Cyclooxygenase 2 expression in pancreatic adenocarcinoma and pancreatic intraepithelial neoplasia: an immuno-histo-chemical analysis with automated cellular imaging," Am J Clin Pathol 118(2), 194-201 (2002).

Matsubayashi H., Sato N., Brune K., Lapides A., Blackford, Hruban R. H., Canto M., Yeo C. J., and Goggin M. "Age— and Disease-Related Methylation of Multiple Genes in Non-neoplastic Duodenum and in Duodenal Juice," Clinical Cancer Res. 11, 573-583 (2005).

Mott N. F. & Twose W. D. "The Theory of impurity conduction." Adv. Phys. 10, 107-163 (1961).

Murr M. M., Sarr M. G., Oishi A. J., and e. al., "Pancreatic cancer," CA Cancer J Clin 44(5), 304-3 18 (1994).

Perelman L. T. et al. "Observation of periodic fine structure in reflectance from biological tissue: A new technique for measuring nuclear size distribution." Phys. Rev. Lett. 80, 627-630 (1998).

Pradhan P. & Kumar N. "Localization of light in coherently amplifying random media." Phys. Rev. B 50, 9644-9647 (1994).

Rammal R. & Doucot B. "Invariant imbedding approach to localization .1. General framework and basic equations." Journal De Physique 48, 509-526 (1987).

Richards B. & Wolf E. "Electromagnetic diffraction in optical systems .2. Structure of the image field in an aplanatic system." Proceedings of the Royal Society of London Series a-Mathematical and Physical Sciences 253, 358-379 (1959).

Robbins S. L., Kumar V., Abbas A. K., Fausto N. & Cotran R. S. "Robbins and Cotran pathologic basis of disease, xv" Saunders, Philadelphia, 1525 (2004).

Roy H. K., Liu Y., Wali R. K., Kim Y. L., Kromine A. K., Goldberg M. J., and Backman V., Gastroenterology 126, 1071 (2004).

Roy H. K., Iversen P., Hart J., Liu Y., Koetsier J. L., Kim Y., Kunte D. P., Madugula M., Backman V., and Wall R. K. "Down regulation of SNAIL Suppresses MIN Mouse Tumorigenesis: Modulation of Apoptosis, Proliferation and Fractal Dimension," Molecular Cancer Therapeutics 3(9), 1159-1165 (2004).

Roy H. K., Kim Y. L., Liu Y., Wali R. K., Goldberg M. J., Turzhitsky V., Horwits J., and Backman V. "Risk-Stratification of Colon Carcinogenesis through Enhanced Backscattering (EBS) Spectroscopy Analysis of the Uninvolved Colonic Mucosa," Clin Cancer Res, submitted (2005).

Roy H. K., Kim Y. L., Wali R. K., Liu Y., Koetsier J. L., Kromine A., Kunte D. P., Goldberg M. J., and Backman V. "Spectral Markers in the Preneoplastic MIN Mouse Intestinal Mucosa Accurately Identify Germline Status and Chemo preventive Effect of Celecoxib," Cancer Epidemiology, Biomarkers & Prevention 14(7), 1639-1645 (2005).

Roy H., Wall R., Kim Y., Liu Y., Goldberg M., and Backman V. "Four-Dimensional Elastic Light-Scattering Fingerprints as Preneoplastic Markers in the Rat Model of Colon Carcinogenesis," Gastroenterology 126, 1071-1081 (2004).

Roy H., Wali R., Kim Y., Liu Y., Goldberg M., Kromine A., Chen K., and Backman V. "Early Detection of Experimental Colon Carcinogenesis Utilizing Light Scattering Spectroscopy (LSS)," Gastroenterology 124(4), Supp. 1, A-5 (2003).

Saisho H., and Yamaguchi T. "Diagnostic imaging for pancreatic cancer: computed tomography, magnetic resonance imaging, and positron emission tomography," Pancreas 28(3), 273-278 (2004).

Schmitt J. M. & Kumar G. "Optical scattering properties of soft tissue: a discrete particle model." Appl. Optics 37, 2788-2797 (1998).

Schrock E., du Manoir S., Veldman T., Schoell B., Wienberg J., Ferguson-Smith M. A., Ning Y., Ledbetter D. H., Bar-Am I., Soenksen D., Garini Y., and Ried T., Science 273, 494 (1996).

Schuele G., Vitkin E., Huie P., O'Conell-Rodwell C., Palanker D., and Perelman D. L. T. "Optical spectroscopy non-invasively monitors response of organelles to cellular stress," J. Biomed. Opt. (to be published).

Shamsuddin A. N., Tyner G. T., and Yang G. Y. "Common expression of the tumor marker D-galactose-beta-[1-≦3]-N-acetyl-D-galactosamine by different adenocarcinomas: evidence of field effect phenomenon," Cancer Res. 55(1), 149-152 (1995).

Siegel M. P., Kim Y. L., Roy H., Wali R., and Backman V. "Assessment of Blood Supply in Superficial Tissue using Polarization Gated Elastic Light Scattering Spectroscopy," Appl Optics, accepted (2006).

Stephens D. J. & Allan V. J. "Light microscopy techniques for live cell imaging." Science 300, 82-86 (2003).

Subramanian H., Pradhan P., Kim Y. L., Liu Y., and Backman V. "Photon random walk model of low-coherence enhanced backscattering (LEBS) from anisotropic disordered media: a Monte Carlo simulation," Applied Optics, submitted (2005).

Taflove A. & Hagness S. C. "Computational Electrodynamics : The Finite-Difference Time-Domain Method, 3rd edition. Computational Electrodynamics : The Finite-Difference Time-Domain Method," 3rd edition Artech House, Norwood, MA, (2005).

Taflove A. and Hagness S. C., "Computational Electrodynamics: the Finite-Difference Time-Domain Method. Artech (2000).

Uehara H., Nakaizumi A., Tatsuta M., and e. al., "Diagnosis of carcinoma in Situ of the pancreas by per oral pancreatscopy and pancreatoscopic cytology," Cancer 79, 454-460 (1997).

Umashankar K. R. & Taflove A. "A novel method to analyze electromagnetic scattering of complex objects." IEEE Trans. Electromagnetic Compatibility 24, 397-405 (1982).

Valentine M. T., Popp A. K., Weitz D. A., and Kaplan P. D., Opt. Lett. 26, 890 (2001).

van de Hulst H. C., "Light Scattering by Small Particles" Dover (1981).

van Rossum M. C. W., Lerner I. V., Altshuler B. L. & Nieuwenhuizen T. M. "Deviations from the Gaussian distribution of mesoscopic conductance fluctuations." Phys. Rev. B 55, 4710-4716 (1997).

Wali R. K., Baum C. L., Sitrin M. D. & Brasitus T. A. "1,25 (Oh)2 Vitamin-D3 Stimulates Membrane Phosphoinositide Turnover, Activates Protein Kinase-C, and Increases Cytosolic Calcium in Rat Colonic Epithelium." Journal of Clinical Investigation 85, 1296-1303 (1990).

Wali R. K., Roy H. K., Kim Y. L., Liu Y., Koetsier J. L., Kunte D. P., Goldberg M. J., Turzhitsky V., and Backman V. "Increased Microvascular Blood Content is an Early Event in Colon Carcinogenesis," Gut 54, 654-660 (2005).

Wali R., Roy H., Kim Y., Liu Y., Goldberg M., Kromine A., Chen K., and Backman V. "Increased Mucosal Blood Flow is an Early Marker of Colon Carcinogenesis," Gastroenterology 124(4), Supp. 1, A-4 (2003).

Watanabe H., Yamaguchi Y., Ha A., and e. al., "Quantitative determination of K-ras mutations in pancreatic juice for diagnosis of pancreatic cancer using hybridization protection assay," Pancreas 17, 341-347 (1998).

Wax A. et al. "In situ detection of neoplastic transformation and chemo preventive effects in rat esophagus epithelium using angle-resolved low-coherence interferometry." Cancer Res. 63, 3556-3559 (2003).

Wax A., Yang C. H., and Izatt J. A., Opt. Lea. 28, 1230 (2003).

Wax A. et al. "In situ detection of neoplastic transformation and chemo preventive effects in rat esophagus epithelium using angle-resolved low-coherence interferometry." Cancer Research 63, 3556-3559 (2003).

Willett C. G., Boucher Y., di Tomaso E., Duda D. G., Munn L. L., Tong R. T., Chung D. C., Sahani D. V., Kalva S. P., Kozin S. V., Mino M., Cohen K. S., Scadden D. T., Hartford A. C., Fischman A. J., Clark J. W., Ryan D. P., Zhu A. X., Blaszkowsky L. S., Chen H. X., Shellito P. C. Lauwers G. Y., and Jam R. K. "Direct evidence that the VEGF—specific antibody bevacizumab has anti vascular effects in human rectal cancer," Nat Med 10(2), 145-147 (2004).

Yasuda K., Mukai H., and Nakajima M. "Endoscopic ultrasonography diagnosis of pancreatic cancer," Gastrointestinal Endosc Clin N Am 5(4), 699-712 (1995).

Zumbusch A., Holtom G. R., & Xie X. S. "Three-dimensional vibrational imaging by coherent anti-Stokes Raman scattering." Phys. Rev. Lett. 82, 4142-4145 (1999).

The invention claimed is:

1. A system to illuminate a target to determine refractive index fluctuations within the target, comprising:
   a light source to provide a broad spectrum of incident light on the target; and
   a receiving end positioned in the imaging plane of the system to separately record the intensity of multiple preselected spectra of one of backscattered or through-transmitted light emerging from one or more preselected areas of the target illuminated with the incident light, the multiple preselected spectra of emergent light resulting from refractive index fluctuations within the target.

2. The system of claim 1, wherein the diameter of a beam of light illuminated on the target is substantially larger than a size of the target such that the beam of light illuminated on the target corresponds to a plane wave.

3. The system of claim 1, wherein the light source comprises a white light source.

4. The system of claim 1, wherein the light source obtains the broad spectrum of light from a plurality of narrowband light sources.

5. The system of claim 1, wherein the light source comprises one or more lasers with one or more wavelengths of emission.

6. The system of claim 1, wherein the light source comprises one or more light emitting diodes with one or more spectral emission ranges.

7. The system of claim 1, further comprising a wavelength selectable optical filter disposed between the light source and the receiving end.

8. The system of claim 1, wherein the receiving end comprises an imaging spectrograph capable of receiving at least two distinct spectra within the broad spectrum of incident light provided by the light source.

9. The system of claim 8, wherein the illumination source provides, and the receiving end receives, a substantial portion of the human-visible spectrum.

10. The system of claim 1, further comprising a light detector coupled with an imaging spectrograph, and a scanning stage coupled with the imaging spectrograph and the light detector, the scanning stage operatively configured to move about a predetermined position.

11. The system of claim 10, wherein the light detector is a CCD camera.

12. The system of claim 10, wherein the light detector is a plurality of photodetectors.

13. The system of claim 1, wherein the target comprises one or more living cells of a biological sample with a thickness less than the mean free path of light in the sample.

14. The system of claim 1, wherein the receiving end further comprises one or more single channel linear-array spectrometers.

15. The system of claim 1, wherein the one or more preselected areas of the target are microscopic.

16. The system of claim 15, wherein the incident light is configured to propagate through the microscopic target in substantially one dimension.

17. The system of claim 15, further comprising one or more optical components operatively configured to focus the incident light on the microscopic target.

18. The system of claim 15, further comprising one or more optical components operatively configured to magnify the light emerging from the microscopic target for recordation by the receiving end.

19. The system of claim 1, wherein the one or more preselected areas of the target are about the size of the longest wavelength of the received spectra.

20. The system of claim 1, wherein the receiving end records spectral information on a cell by cell basis.

* * * * *